(12) United States Patent
Francischetti et al.

(10) Patent No.: US 8,772,238 B2
(45) Date of Patent: Jul. 8, 2014

(54) USE OF IXOLARIS, A TISSUE FACTOR INHIBITOR, FOR THE TREATMENT OF CANCER

(75) Inventors: Ivo M. B. Francischetti, Bethesda, MD (US); Robson de Queiroz Monteiro, Rio de Janeiro (BR); Jose Marcos C. Ribeiro, Rockville, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/257,455

(22) PCT Filed: Mar. 18, 2010

(86) PCT No.: PCT/US2010/027797
§ 371 (c)(1),
(2), (4) Date: Sep. 19, 2011

(87) PCT Pub. No.: WO2010/107991
PCT Pub. Date: Sep. 23, 2010

(65) Prior Publication Data
US 2012/0010137 A1   Jan. 12, 2012

Related U.S. Application Data

(60) Provisional application No. 61/161,223, filed on Mar. 18, 2009, provisional application No. 61/225,961, filed on Jul. 16, 2009.

(51) Int. Cl.
*A61K 38/57* (2006.01)
*A61K 38/00* (2006.01)
*C07K 14/00* (2006.01)

(52) U.S. Cl.
USPC ........ 514/14.5; 514/17.7; 514/19.3; 435/325; 530/350

(58) Field of Classification Search
None
See application file for complete search history.

(56) References Cited

U.S. PATENT DOCUMENTS

| | | | | |
|---|---|---|---|---|
| 6,734,163 | B2 * | 5/2004 | Papathanassiu et al. | 514/13.3 |
| 7,078,508 | B2 * | 7/2006 | Francischetti et al. | 536/23.1 |
| 2009/0042786 | A1 * | 2/2009 | Maria et al. | 514/12 |

FOREIGN PATENT DOCUMENTS

| | | |
|---|---|---|
| WO | 0233089 A2 | 4/2002 |
| WO | 2009009399 A2 | 1/2009 |

OTHER PUBLICATIONS

Pub Med search. Jul. 3, 2013.*
Carneiro-Lobo et al., "PO-62 Procoagulant properties of U87MG human glioblastoma cells and molecular targets of the anticoagulant and antitumor agent Ixolaris", Thrombosis Research, vol. 120, p. S165 (2007).
Hua et al., "The role of thrombin in gliomas", Journal of Thrombosis and Haemostasis, vol. 3, No. 9, pp. 1917-1923 (2005).
Milsom et al., "Tissue Factor Regulation by Epidermal Growth Factor Receptor and Epithelial-to-Mesenchymal Transitions: Effect on Tumor Initiation and Angiogenesis", Cancer Research, vol. 68, No. 4, pp. 10068-10076 (2008).
Konduri et al., "Role of tissue factor pathway inhibitor-2 (TFPI-2) in amelanotic melanoma (C-32) invasion", Clinical & Experimental Metastasis Research Society, vol. 18, No. 4, pp. 303-308 (2000).
Carneiro-Lobo et al., "Ixolaris, a tissue factor inhibitor, blocks primary tumor growth and angiogenesis in a glioblastoma model", Journal of Thrombosis and Haemostasis, vol. 7, No. 11, pp. 1855-1864 (2009).

* cited by examiner

*Primary Examiner* — Elly-Gerald Stoica
(74) *Attorney, Agent, or Firm* — Edwards Wildman Palmer LLP; Peter F. Corless

(57) ABSTRACT

The invention provides methods for treatment of tissue factor (TF) mediated or associated diseases or processes, such as cancer, by administering at least an active fragment of an Ixolaris polypeptide to a subject. The invention further includes identification of a subject in need of such treatment, and monitoring a subject for amelioration of at least one sign or symptom of the disease. The invention also features kits.

21 Claims, 5 Drawing Sheets

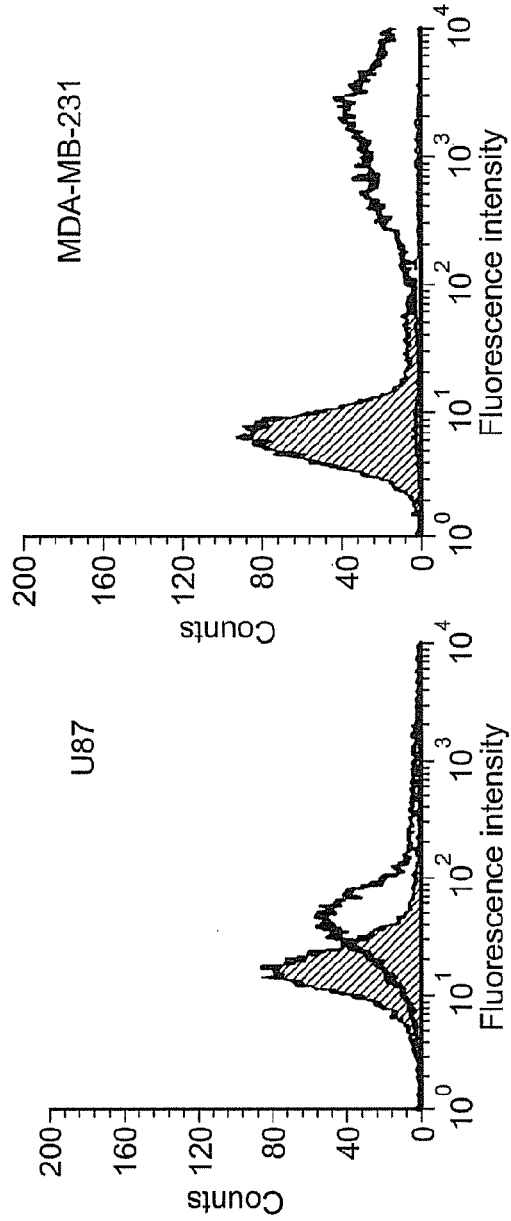
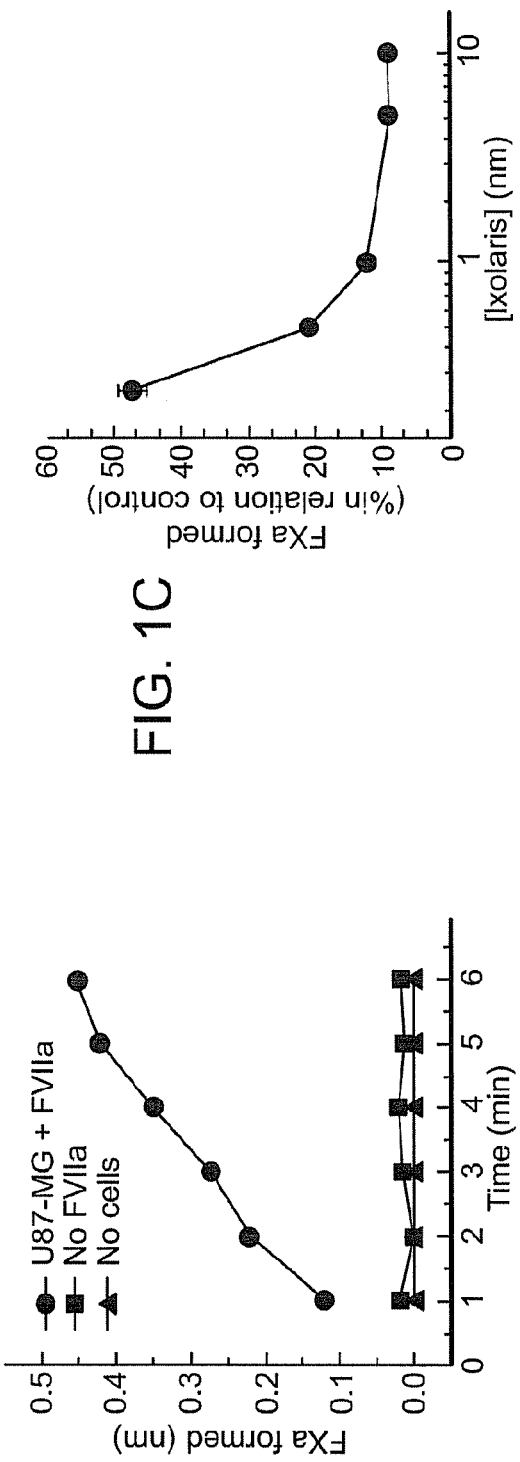
FIG. 1A
FIG. 1B
FIG. 1C

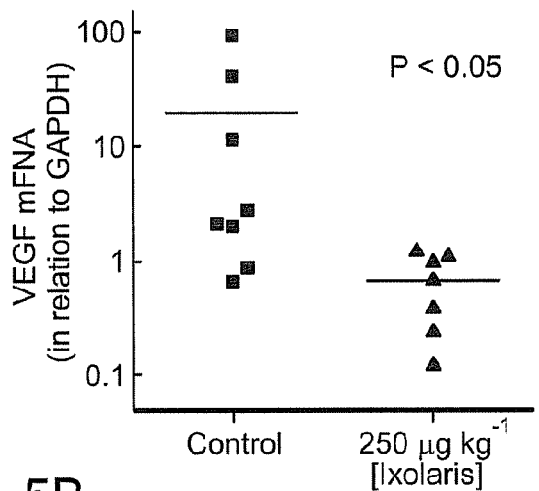
FIG. 5A

FIG. 5D
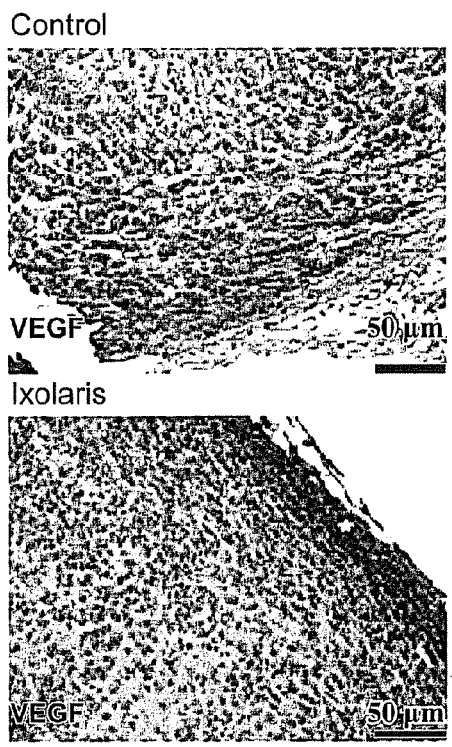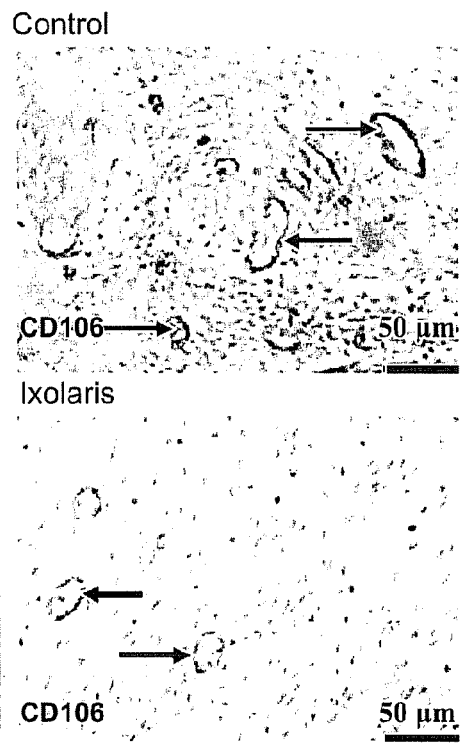

USE OF IXOLARIS, A TISSUE FACTOR INHIBITOR, FOR THE TREATMENT OF CANCER

CROSS-REFERENCE TO RELATED APPLICATIONS

This application is a 35 U.S.C. §371 U.S. national entry of International Application PCT/US2010/027797 (WO 2010/107991) having an International filing date of Mar. 18, 2010, which claims the benefit of U.S. Provisional Application No. 61/161,223, filed Mar. 18, 2009 and 61/225,961, filed Jul. 16, 2009. The entire contents of the aforementioned applications are hereby incorporated by reference.

GOVERNMENT SUPPORT

The following invention was supported at least in part by grant from the National Institute of Health. Accordingly, the government has certain rights in the invention.

BACKGROUND OF THE INVENTION

Malignant gliomas are very aggressive cancers, displaying high rates of mortality (within months) and resistance to therapeutic interventions. Levels of tissue factor (TF) expression have been shown to correlate with the histological grade of malignancy and vascularity in a number of cancer types, including glioblastoma. Further, TF is overexpressed around the typical necrotic foci found in glioblastoma [20]. These regions are highly hypoxic and seem to play a key role in glioblastoma aggressiveness, presenting an increased production of VEGF, IL-8 and metalloproteases [21,22].

Ixolaris, a tick salivary 140 amino acid protein containing 10 cysteines and 2 Kunitz-like domains, binds to FXa or FX as a scaffold for inhibition of the TF/FVIIa complex, in which the FVIIa catalytic site is inactivated. In contrast to TFPI, however, Ixolaris does not bind to the active site cleft of FXa. Instead, complex formation is mediated by the FXa heparin-binding exosite [26]. In addition, Ixolaris interacts with zymogen FX through a precursor state of the heparin-binding exosite [27]. Because Ixolaris displays potent and long-lasting antithrombotic activity this molecule might interfere with glioblastoma progression.

Inhibition or targeting of TF may therefore provide an anti-tumor strategy that could affect the survival of TF overexpressing tumor cells by inhibiting TF mediated cellular signaling or other activities. Further, this approach may prevent tumor growth indirectly via an antiangiogenic mechanism by inhibiting the growth or function of TF expressing intra-tumoral endothelial cells.

The present invention is directed to novel therapies for TF mediated or associated diseases or processes, and in particular cancer and vascular diseases.

SUMMARY OF THE INVENTION

The present invention is based, at least in part, on work by the present inventors who found that the tick anticoagulant Ixolaris blocked tissue factor (TF) dependent procoagulant activity of human glioblastoma and melanoma cell lines and attenuated multimolecular coagulation complex assembly. The present inventors have found that Ixolaris inhibits in vivo tumorigenic potential of human glioblastoma and melanoma cells in nude mice, without observable bleeding, and was associated with reduced tumor vascularization and VEGF expression. Accordingly, the present inventors describe Ixolaris as a promising agent for anti-tumor therapy.

In a first aspect, the present invention features a method of inhibiting growth of a cell expressing tissue factor (TF), comprising contacting the cell with an effective amount of a tissue factor pathway inhibitor (TFPI) compound, such that the growth of the cell is inhibited.

In another aspect, the present invention features a method of treating or preventing a TF mediated or associated disease or process in a subject, comprising administering to the subject a TFPI compound in an amount effective to treat or prevent the TF mediated or associated disease or process.

In another further aspect, the present invention features a method of treating or preventing the growth or metastasis of tumor cells in a subject, comprising administering to the subject a TFPI compound in an amount effective to treat or prevent the growth or metastasis of the tumor cells.

In one embodiment, the cells are selected from tumor cells, endothelial cells, vascular smooth muscle cells, inflammatory cells, or a combination thereof.

In another embodiment of the above aspects, the TFPI compound comprises a tick saliva protein.

In another further embodiments, the TFPI compound comprises at least an active fragment of an Ixolaris polypeptide.

In still another embodiments, the disease is selected from the group consisting of: cancer and a vascular disease.

In another embodiment, the tumor comprises a solid tumor.

In still another embodiment, the tumor comprises a central nervous system tumor or a squamous cell tumor.

In another embodiment, the tumor is a glioblastoma.

In still another embodiment, the tumor is a melanoma.

In another embodiment of any one of the above aspects, the tumor is a metastatic tumor.

In still another embodiment, treating or preventing the growth of tumor cells comprises at least one selected from the group consisting of: decreasing the rate of tumor growth, stopping tumor growth, shrinking the tumor, lessening tumor burden, preventing metastasis, or reducing at least one sign or symptom associated with the presence of a tumor.

In another embodiment, the one or more tumor markers are a sign or symptom associated with the presence of a tumor.

In another aspect, the invention features a method of treating or preventing a vascular disease in a subject comprising administering to the subject a TFPI compound in an amount effective to treat or prevent the vascular disease.

In one embodiment, the TFPI compound comprises a tick saliva protein.

In another embodiment, the TFPI compound comprises at least an active fragment of an Ixolaris polypeptide.

In still another embodiment, the vascular disease is selected from diabetic retinopathy, age-related macular degeneration, and pulmonary hypertension.

In another embodiment, administering a tick saliva protein inhibits angiogenesis in the subject.

In another preferred embodiment of any one of the above aspects, the TFPI compound is administered in combination concurrently or sequentially with another agent.

In another further embodiment, the agent is selected a cytotoxic agent, an anti-neoplastic agent, an immunosuppressive, and a VEGF antagonist.

In another preferred embodiment of any one of the above aspects, the method further comprises identifying a subject in need of treatment with a TFPI compound.

In still another preferred embodiment of any one of the above aspects, the method further comprises monitoring a subject for effects of treatment with TFPI compound.

In another aspect, the invention features a method of treating or preventing cancer in a subject comprising administering to the subject a TFPI compound in an amount effective to treat or prevent cancer.

In one embodiment, the TFPI compound comprises a tick saliva protein.

In another embodiment, the TFPI compound comprises at least an active fragment of an Ixolaris polypeptide.

In a further embodiment of the above aspects, the method further comprises monitoring the subject for amelioration of at least one sign or symptom of cancer.

In still another embodiment of the above aspects, the cancer comprises a tumor with high expression or production of one or more proteins selected from tissue factor (TF), Factor VIIa, Factor Xa, thrombin, vascular endothelial growth factor (VEGF), interleukin-8 (IL-8), one or more matrix metalloproteases, Factor VII, and Factor X, as compared to a control cell not derived from the tumor.

In another embodiment of the above aspects, the cancer comprises a tumor wherein the tumor expresses TF around the necrotic core.

In still another embodiment of the above aspects, the tumor is a highly vascularized tumor.

In still another embodiment of the above aspects, the tumor comprises a glioblastoma.

In another embodiment of the above aspects, an active fragment of an Ixolaris polypeptide comprises at least 40 contiguous amino acids or more, 50 contiguous amino acids or more, 60 contiguous amino acids or more, 70 contiguous amino acids or more, 80 contiguous amino acids or more, 90 contiguous amino acids or more, 100 contiguous amino acids or more, 110 contiguous amino acids or more, 120 contiguous amino acids or more, 130 contiguous amino acids or more, 140 contiguous amino acids or more, 150 contiguous amino acids or more, 160 contiguous amino acids or more, or the full length sequence of the amino acid sequence corresponding to SEQ ID NO: 2.

In another embodiment of the above aspects, an active Ixolaris polypeptide comprises at least 80% overall identity or more, 85% overall identity or more, 90% overall identity or more, 95% overall identity or more to a fragment of at least 50 contiguous amino acids of SEQ ID NO: 2.

In another embodiment, amelioration of at least one sign or symptom of cancer comprises at least one of a reduction in tumor volume or a reduction of expression or production of at least one of tissue factor (TF), Factor VIIa, Factor Xa, thrombin, vascular endothelial growth factor (VEGF), IL-8, one or more matrix metalloproteases, Factor VII, or Factor X as compared to prior to treatment with an Ixolaris polypeptide.

In another further embodiment, a reduction in tumor volume comprises a reduction of 20% or more, 30% or more, 40% or more, 50% or more, 60% or more, 70% or more, 80% or more, or 90% or more.

In still another embodiment of the above aspects, the active fragment of an Ixolaris polypeptide comprises administration of a nucleic acid encoding the active fragment of an Ixolaris polypeptide operably linked to control sequences for expression of the polypeptide.

In another embodiment of the above aspects, the method further comprises administration of a an agent for treatment of excess angiogenesis.

In still another embodiment of the above aspects, the method further comprises obtaining an Ixolaris polypeptide.

In another embodiment of the above aspects, the active fragment of the Ixolaris polypeptide is administered at a daily dose of about 1 µg/kg to about 1000 µg/kg, about 10 µg/kg to about 500 µg/kg, about 10 µg/kg to about 750 µg/kg, about 25 µg/kg to about 1000 µg/kg, about 50 µg/kg to about 1000 µg/kg, about 50 µg/kg to about 500 µg/kg, about 25 µg/kg to about 500 µg/kg, or about 25 µg/kg to about 250 µg/kg.

In another further embodiment of the above aspects, the active fragment of the Ixolaris polypeptide is administered one time or more, two times or more, three times or more, four times or more, five times or more, six times or more, seven times or more, eight times or more, ten times or more, fifteen times or more, twenty times or more, or twenty five times or more.

In still another embodiment of the above aspects, the Ixolaris polypeptide is an isolated polypeptide.

The invention also features in preferred embodiments, a pharmaceutical composition for practicing any of the methods of the aspects described herein.

In another aspect, the invention features a pharmaceutical composition comprising an isolated Ixolaris polypeptide in a pharmaceutical excipient.

In another further embodiment, the invention features an antibody that recognizes one or more epitope of a TFPI compound.

In one embodiment, the TFPI compound comprises a tick saliva protein.

In another embodiment, the TFPI compound comprises at least an active fragment of an Ixolaris polypeptide.

In another aspect, the invention provides a kit for practicing any of the methods of the aspects described herein, and instructions for use.

In one embodiment, the kit comprises a TFPI compound.

In another embodiment, the TFPI compound comprises a tick saliva protein.

In another further embodiment, the TFPI compound comprises at least an active fragment of an Ixolaris polypeptide.

DESCRIPTION OF THE DRAWINGS

FIG. 1(A-C) are graphs that show functional TF expressed by U87-MG cells is inhibited by Ixolaris. (A) Expression of TF on U87-MG (left) and MDA-MB-231 (right) cells was evaluated by flow-cytometric analysis. Dashed line represents staining with monoclonal anti-human TF antibody, followed by FITC-conjugated secondary antibody. Grey region represents control in the absence of primary antibody. (B) Assembly of extrinsic tenase complex on U87-MG cells. Kinetics for the activation of FX (100 nM) in the presence of FVIIa (1 nM) and U87-MG cells ($5 \times 10^5$ mL$^{-1}$) (●). Controls were performed in the presence of cells ($5 \times 10^5$ mL$^{-1}$) and absence of FVIIa (■) or in the absence of cells and presence of FVIIa (1 nM) (▲). (C) Inhibitory effect of Ixolaris. FX (100 nM) was incubated for 5 min with the indicated concentrations of Ixolaris prior to activation by FVIIa (1 nM) and U87-MGcells ($5 \times 10^5$ mL$^{-1}$). The conditions for the assays and for quantification of Xa are described in the Materials and methods section. Each point represents mean±SD of three determinations.

DETAILED DESCRIPTION OF THE INVENTION

Definitions

Figure 2A:
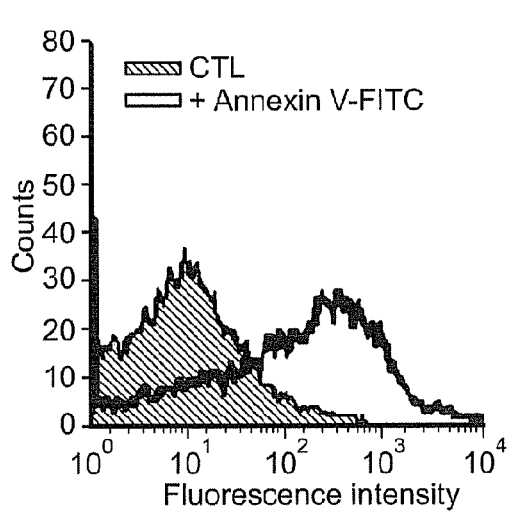
FIG. 2(A-F) are four graphs that show ixolaris inhibits PS-dependent procoagulant complexes assembled on U87-MG cells. Assembly of PS-dependent procoagulant complexes on U87-MG cells. (A) PS exposure on U87-MG was evaluated by flow-cytometric analysis of annexin V binding to cells. Dashed line represents staining with FITC-labeled annexin V. Grey region represents control performed in the absence of annexin V. (B) Assembly of intrinsic tenase complex on U87-MG cells. Kinetics for the activation of FX (100 nM) in the presence of FIXa (0.2 nM), FVIIIa (4 IU mL$^{-1}$) and (●) U87-MG cells ($5 \times 10^5$ mL$^{-1}$). Controls were performed in the absence of cells (s). Assay conditions and quantification of Xa are described in the Materials and methods section. Each point represents mean±SD of three determinations. (C) Prothrombinase complex assembly on U87-MG cells. (A) Kinetics for the activation of prothrombin (0.5 lM) in the presence of FXa (10 pM), FVa (1 nM) and U87-MG cells (5·105 cells mL$^{-1}$ (■). Controls were performed in the absence of cells (□). Assay conditions and quantification of thrombin are described in the Materials and methods section. Each point represents mean±SD of three determinations. (D) Inhibitory effect of annexin V on FX (●) or prothrombin activation (■). U87-MG cells (5×10$^5$ mL$^{-1}$) were incubated with the indicated concentrations of annexin V prior to addition of either FXa (10 pM)/prothrombin (0.5 IM) or FIXa (0.2 nM)/FX (100 nM), followed by addition of FVa (1 nM) or FVIIIa (4 IU mL$^{-1}$), respectively. Zymogen activation rates in the absence of annexin V were taken as 100%. Assay conditions are described in the Materials and methods section. Each point represents mean±SD of three determinations. (E) Activation of FX (100 nM) by FIXa (0.2 nM), FVIIIa (4 U mL$^{-1}$) and U87-MG cells (5×10$^5$ mL$^{-1}$) was assayed at the indicated concentrations of Ixolaris. (F) Prothrombin (0.5 μM) activation by FXa (10 μM) in the presence of FVa (1 nM) and U87-MG cells (5×10$^5$ mL$^{-1}$) was assayed at the indicated concentrations of Ixolaris. Assay conditions are described in the Materials and methods section. Each point represents mean±SD of three determinations.
Figure 2B:
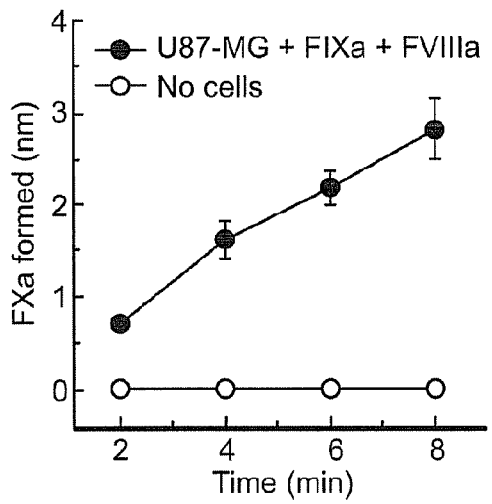
Figure 2C:
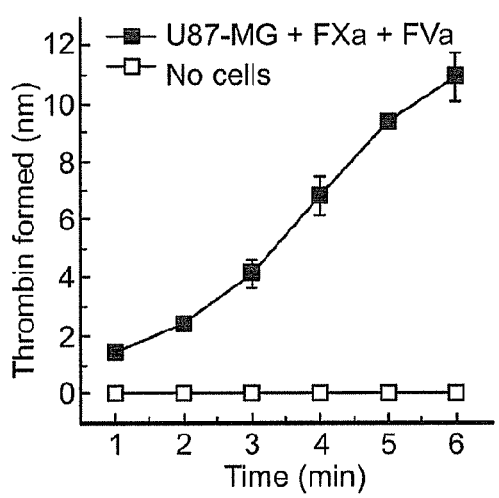

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3,4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

As used herein, the term "cancer" is used to mean a condition in which a cell in a patient's body undergoes abnormal, uncontrolled proliferation. Thus, "cancer" is a cell-proliferative disorder. "Cancer" as used herein is understood as any of a class of diseases in which a group of cells display uncontrolled growth (division beyond the normal limits), invasion (intrusion on and destruction of adjacent tissues), and sometimes metastasis (spread to other locations in the body via lymph or blood). Cancers can be divided into two large groups of solid tumors and non-solid tumors (e.g., blood tumors such as leukemias). Cancer can occur in nearly any tissue of the body including, but not limited to adrenocortical carcinoma, anal cancer, bladder cancer, brain stem glioma, brain tumors, breast cancer, cerebellar astrocytoma/malignant glioma, cervical cancer, chronic myeloproliferative disorders, colon cancer, endometrial cancer, ependymoma, esophageal cancer, Ewing family of tumors, extracranial germ cell tumors, extragonadal germ cell tumors, extrahepatic bile duct cancer, gallbladder cancer, gastric cancer, gastrointestinal carcinoid tumors, gestational trophoblastic tumors, hypopharyngeal cancer, islet cell carcinoma (Endocrine Pancreas), islet cell tumors (endocrine pancreas), laryngeal cancer, leukemia, acute lymphoblastic; leukemia, acute myeloid; leukemia, chronic lymphocytic; leukemia, chronic Myelogenous, lip and oral cavity cancer, liver cancer, lung cancer, non-small cell; lung cancer, small cell, lymphoma, Hodgkin's, lymphoma, Non-Hodgkin's, lymphoma, AIDS-Related, lymphoma, lymphoma, primary CNS, melanoma, intraocular (Eye), medulloblastoma, Merkel cell carcinoma, mesothelioma, mycosis fungoides and the Sézary Syndrome, myelodysplastic and myeloproliferative diseases, myelodysplastic Syndromes, myeloid leukemia/other myeloid cancers, nasopharyngeal cancer, neuroblastoma, oropharyngeal cancer, osteosarcoma/malignant fibrous histiocytoma of bone, ovarian epithelial cancer, ovarian germ cell tumors, pancreatic cancer, paranasal sinus and nasal cavity cancer, parathyroid cancer, penile cancer, pheochromocytoma, pituitary tumors, prostate cancer, rectal cancer, renal cell cancer, retinoblastoma, rhabdomyosarcoma, salivary gland cancer, sarcoma, soft Tissue, sarcoma, Kaposi, skin cancer, small Intestine cancer, squamous neck cancer with occult primary, supratentorial primitive neuroectodermal tumors and pineoblastoma, testicular cancer, thymoma and thymic carcinoma, thyroid cancer, transitional cell cancer of the renal pelvis and ureter, urethral cancer, uterine sarcoma, vaginal cancer, visual pathway and hypothalamic glioma, and vulvar cancer.

As used herein "amelioration" or "treatment" is understood as meaning to lessen or decrease at least one sign, symptom, indication, or effect of a specific disease or condition. For example, amelioration or treatment of cancer can include preventing of the formation of tumors, shrinking one or more tumors, limiting or preventing the formation of metastases. As used herein, "prevention" is understood as to delay, limit, reduce the rate or degree of onset, or inhibit the development of at least one sign or symptom of a disease or condition. Prevention, amelioration, and treatment can require administration of one or more doses of at least an active fragment of an ixolaris polypeptide.

As used herein, "contacting a cell" is meant to refer to providing an agent to a cell, in culture or in an animal, such that the agent can interact with the surface of the cell, potentially be taken up by the cell, and have an effect on the cell. The agent can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "detecting", "detection" and the like are understood that an assay performed for identification of a specific analyte in a sample or a change in a subject of at least one sign or symptom of a disease, expression of a protein or gene, including a reporter construct. The amount of analyte detected in the sample or change of behavior in a subject can be none or below the level of detection of the assay or method.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in a heterologous system). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. Isolated cells can be further modified to include reporter constructs or be treated with various stimuli to modulate expression of a gene of interest.

As used herein, "ixolaris" is understood as the amino acid and polypeptide sequence provided at GenBank Accession No. (GenBank: AF286029.1) and described in US Patent Publication 20040018516 (incorporated herein by reference). At least an active fragment of an ixolaris polypeptide is understood as a polypeptide that has at least 20%, at least 30%, at least 40%, at least 50%, at least 60%, at least 70%, at least 80%, at least 90%, at least 95% of the inhibitory activity of a wild-type, full length ixolaris polypeptide or a mature processed 140 amino acid ixolaris polypeptide in a TF-mediated coagulant activity assay such as that provided herein, or any of the other assays provided herein to test ixolaris activity such as Factor X generation assay, the thrombin generation assay, the inhibition of formation of coagulation complexes by annexin V, or modification of coagulation time. An active fragment of an ixolaris polypeptide includes at least 40 contiguous amino acids, 50 contiguous amino acids, 60 contiguous amino acids, 70 contiguous amino acids, 80 contiguous amino acids, 90 contiguous amino acids, 100 contiguous amino acids, 110 contiguous amino acids, 120 contiguous amino acids, 130 contiguous amino acids, 140 contiguous amino acids, 150 contiguous amino acids, 160 contiguous amino acids of the amino acid sequence provided by GenBank: AF286029.1. An active ixolaris polypeptide has at least 80%, at least 85%, at least 90%, at least 95% overall identity to a fragment of at least 50 contiguous amino acids of GenBank: AF286029.1.

As used herein, "kits" are understood to contain at least the non-standard laboratory reagents for use in the methods of the invention, such as a ixolaris polypeptide or amino acid coding sequence. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

As used herein, the term "obtaining" is understood to refer to manufacturing, purchasing, or otherwise coming into possession of.

"Peptide", "polypeptide", "protein", and the like are understood as two or more naturally occurring or synthetic amino acids joined by an amide linkage. Optionally the peptide further includes one or more modifications such as modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins, Structure and Molecular Properties, 2nd ed., T. E. Creighton, W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-646 (1990); Rattan et al., Ann. N.Y. Acad. Sci. 663: 48-62 (1992)).

As used herein, the phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As used herein, the term "subject" is meant to refer to living organisms. In certain embodiments, the living organism is an animal. In certain preferred embodiments, the subject is a mammal. In certain embodiments, the subject is a domesticated mammal. Examples of subjects include humans, non-human primates, dogs, cats, mice, rats, cows, horses, goats, and sheep. A human subject may also be referred to as a patient.

A subject "suffering from or suspected of suffering from" a specific disease, condition, or syndrome has at least one risk factor or presents with at least one sign or symptom of the disease, condition, or syndrome such that a competent individual would diagnose or suspect that the subject was suffering from the disease, condition, or syndrome. Methods for identification of subjects suffering from or suspected of suffering from cancer is within the ability of those in the art. Methods of identifying specific genetic or lifestyle predispositions to cancer is well within the ability of those of skill in the art. Subjects suffering from, and suspected of suffering from, a specific disease, condition, or syndrome are not necessarily two distinct groups.

As used herein, the term "therapeutically effective amount," is meant to refer to an amount of an agent which is effective, upon single or multiple dose administration to the cell or subject, decreasing at least one sign or symptom of the disease or disorder, or prolonging the survivability of the patient with such a disease or disorder beyond that expected in the absence of such treatment.

As used herein, the term "tissue factor (TF) protein" is meant to refer to a polypeptide having an amino acid sequence corresponding to a naturally occurring tissue factor, and particularly a mammalian tissue factor or a recombinant tissue factor. Naturally occurring TF includes human species as well as other animal species such as rabbit, rat, porcine, non human primate, equine, murine, and ovine tissue factor (see, for example, Hartzell et al., (1989) Mol. Cell. Biol., 9:2567-2573; Andrews et al., (1991) Gene, 98:265-269; and Takayenik et al., (1991) Biochem. Biophys. Res. Comm., 181: 1145-1150). In certain embodiments, the amino acid sequence of human tissue factor corresponds to NCBI Accession No. NP_001984.1 and is represented by SEQ ID NO: 1-. The amino acid sequences of the other mammalian tissue factor proteins are generally known or obtainable through conventional techniques.

As used herein, "tissue factor (TF) mediated or associated disease or process" according to the present invention is any event which is mediated by the presence of TF. A "TF related disease" is meant to refer to a disease or disorder which may be impacted through the inhibition of TF, particularly the inhibition of tumor growth on tissue factor expressing cells, but also includes other tissue factor mediated diseases such as chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulopathy (DIC) and other diseases.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

As used herein, the term "vascular disease" is meant to refer to any disease or disorder that affects the circulatory system.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Tissue Factor (TF)

The coagulation of blood involves a cascading series of reactions leading to the formation of fibrin. The coagulation cascade consists of two overlapping pathways, both of which are required for hemostasis. The intrinsic pathway comprises protein factors present in circulating blood, while the extrinsic pathway requires tissue factor (TF), which is expressed on the cell surface of a variety of tissues in response to vascular injury. When exposed to blood, TF sets in motion a cascade of activation steps that result in the formation of an insoluble fibrin clot.

TF has been investigated as a target for anticoagulant therapy. TF is a single chain, 263 amino acid membrane glycoprotein that functions as a receptor for factor VII and VIIa and thereby initiates the extrinsic pathway of the coagulation cascade in response to vascular injury. TF is a transmembrane cell surface receptor which serves as the receptor as well as the cofactor for factor VIIa, forming a proteolytically active TF:VIIa complex on cell surfaces.

In certain embodiments, the amino acid sequence of human tissue factor (precursor) corresponds to NCBI Accession No. NP_001984.1 and is represented by SEQ ID NO: 1, shown below:

```
                                              SEQ ID NO: 1
    metpawprvp rpetavartl llgwvfaqva gasgttntva aynltwkstn fktilewepk pvnqvytvqi stksgdwksk cfyttdtecd ltdeivkdvk qtylarvfsy pagnvestgs ageplyensp eftpyletnl gqptiqsfeq vgtkvnvtve dertlvrrnn tflslrdvfg kdliytlyyw kssssgkkta ktntneflid vdkgenycfs vqavipsrtv nrkstdspve cmgqekgefr eifyiigavv fvviilviil aislhkcrka gvgqswkens plnvs
```

Vessel wall injury leads to exposure of membrane-bound tissue factor (TF), which is a crucial step in the initiation of blood coagulation [1]. TF functions as a cofactor for blood coagulation factor VIIa (FVIIa), and the resultant binary FVIIa/TF complex then generates FIXa and FXa. Generation of FIXa by the FVIIa/TF complex results in formation of the tenase complex, following binding to the non-enzymatic cofactor, activated FVIIIa. The tenase complex, along with FVIIa/TF, converts FX to FXa, which assembles with FVa into the prothrombinase complex that is directly responsible for the formation of thrombin [2,3].

Constitutive tissue distribution of TF is highly heterogeneous [4] and its induced and/or deregulated expression has been related to a number of pathological processes [5,6].

Tissue factor is overexpressed on a variety of malignant tumors and isolated human tumor cell lines, suggesting a role in tumor growth and survival. Abnormal elevated TF expression has been well documented in several tumor types, and seems to be directly correlated with thromboembolic complications in cancer patients [7,8]. TF is not produced by healthy endothelial cells lining normal blood vessels but is expressed on these cells in tumor vessels. It appears to play a role in both vasculogenesis, the formation of new blood vessels in the developing animal and in angiogenesis, the sprouting of new capillaries from existing arteries, in normal and malignant adult tissues.

Aberrant expression of TF on endothelial and tumor cells in a variety of breast, colorectal, lung and pancreatic cancers has been linked to an increase in tumor microvessel density and upregulated VEGF expression. Studies employing cultured cells as well as patients' specimens have demonstrated strong correlation between TF expression and aggressive tumor behavior [9-12]. In particular, TF expression correlates with an unbalanced production of anti- and/or proangiogenic factors, such as vascular endothelial growth factor (VEGF), thus favoring increased tumor vascularity [13-16]. Tumor cells over expressing TF are also thought to be responsible for the thrombotic complications associated with cancer.

Pro-tumoral effects of TF and blood clotting enzymes (FVIIa, FXa and thrombin) are intimately related to a group of G protein-coupled receptors named Protease Activated Receptors (PARs). In fact, activation of PARs in cancer cells elicits a vast number of cellular responses, which include migration, invasion, proliferation, metastasis, inhibition of apoptosis, and production of several proaggressive factors such as VEGF, interleukin-8 (IL-8), metalloproteases and others [17,18].

Ixolaris Polypeptides and Nucleic Acids

Saliva of the hard tick, *Ixodes scapularis*, has a repertoire of compounds that counteracts host defenses. The present inventors have previously cloned and expressed the tick tissue factor pathway inhibitor, Ixolaris. Recombinant Ixolaris is a highly specific inhibitor of the extrinsic pathway that blocks generation of Xa by TF/VIIa with an apparent Ki in the pM range (US Patent Application 20040018516, incorporated by reference in its entirety herein).

Ixolaris was cloned from a salivary gland cDNA library of the tick *Ixodes scapularis* was randomly cloned and sequenced, identifying a cDNA with high similarity to rabbit tissue factor pathway inhibitor. The full-length nucleotide and deduced amino acid sequences of *Ixodes* TFPI-like protein are provided in SEQ ID NO: 470 and SEQ ID NO: 471 respectively in US Patent publication 20040018516. The translated protein has a short hydrophobic sequence of 25 amino acids typical of signal peptide and an alanine at the N-terminus, according to Signal P software for prediction of N-terminal of proteins (Nielsen, H. et al. 1997 Protein Eng 10:1-6). The mature protein contains 140 amino acids (15.7 kDa) (SEQ ID NO: 138 of US Patent publication 20040018516), including 10 cysteines and a pI of 4.56. Ixolaris is similar to other members of the Kunitz family of proteins including human TFPI precursor (e value=$4^{-14}$, P10646); lacunin from *Manduca sexta* ($1^{-12}$, AAF04457.1); hepatocyte growth factor pathway inhibitor ($8^{-12}$, AAF02490.1); inter-.alpha.-trypsin inhibitor (bikunin) ($7^{-11}$, P04365); amyloid-precursor-like protein ($1^{-11}$, CAA54906.1); and basic pancreatic trypsin inhibitor (aprotinin, $1^{-05}$, 1510193A).

Ixolaris potently inhibits factor VIIa/TF-induced Factor X activation with an $IC_{50}$ in the pM range. Ixolaris is functionally and structurally distinct from its endogenous counterpart, TFPI (53-55): although the six cysteines that characterize the first Kunitz domain (55) of TFPI are conserved in Ixolaris, only four of six cysteines present in the second Kunitz domain of human TFPI are present. Also, whereas the sixth and the first cysteines that, respectively, terminate and initiate the first and second Kunitz domains in human TFPI are separated by 20 amino acids, only 7 amino acids separate the corresponding cysteines in Ixolaris. Additionally, the Kunitz-type domain 2 in Ixolaris is unusual by containing 4 additional amino acids between the fourth and fifth cysteine residues, making this loop longer than most Kunitz-type family members. Also, the presumed P1 reactive-site residue of the first domain in Ixolaris is Glu, whereas Lys occupies this position in TFPI (53). Ixolaris has a short and basic carboxy terminus but, unlike TFPI, it has only 14 amino acids where the positively charged amino acids are not organized as a cluster. In human TFPI, this basic carboxy terminus has been consistently shown to increase its anticoagulant activity (56, 57) and to shorten its half-life (57). The Ixolaris cDNA also encodes three putative N-linked glycosylation sites, at Asn65, Asn98, and Asn136. Consistent with a calculated mass of 15.7 kDa for the carbohydrate-free protein, we could detect a band of about 15.5 kDa in the gels loaded with recombinant Ixolaris; however, an intense smear was observed in PAGE of Ixolaris at a molecular weight range of about 24 kDa. Accordingly, it is likely that these Asn residues are glycosylated, and this is the most abundant form (>95%) of the secreted recombinant molecule.

In certain embodiments, the amino acid sequence of *Ixodes scapularis* TFPI is shown below and is represented by SEQ ID NO: 2, shown below, corresponding to Genbank Accession AF286029:

```
                                          SEQ ID NO: 2
MRAVSCFLYYGVAWIALGSWGASSSAERVSEMDIYEFESWVSCL

DPEQVTCESQEGTHASYNRKTGQCEEQKGTECGGGENHFETLLKCNES

CNDAPKPPCS

LEVDYGVGRANIPRWYYDTNNATCEMFTYGGITGNKNNFESEEECKET

CKGFSLLKKV

NVTIN
```

The nucleic acid sequence that encodes SEQ ID NO: 2 is shown below, and corresponds to SEQ ID NO: 3.

```
                                          SEQ ID NO: 3
  atgcgcgctg tttcctgctt cctatattat ggagttgctt ggattgcact tggaagttgg ggtgcgtcaa gttcagcaga acgtgttagc gaaatggaca tctatgagtt cgaatcctgg
```

-continued
```
  gtatcttgtc ttgatcccga acaagtaacg tgtgaaagcc aagagggaac gcacgcttca tacaaccgaa aaacgggaca gtgtgaagag caaaagggaa cagagtgtgg aggaggcgag aatcactttg aaactttgtt gaagtgcaac gaatcttgca acgatgctcc gaagccacct gctcgctgg aagtagatta tggtgttgga agagctaaca taccacgatg gtattatgac accaacaatg caacttgcga aatgttcacc tatggggaa taactggcaa taaaaacaat tttgaatccg aggaagagtg taaggaaact tgcaagggtt tttctctgtt aaagaaagta aatgtcacta ttaactga
```

In addition to nucleotide sequences encoding the full-length Ixolaris protein, the present invention may also include nucleotide sequences encoding truncations of the Ixolaris protein that have the desired effects, for example prevent a TF mediated or associated disease or process, prevent the growth or metastasis of tumor cells. The nucleotide sequences encoding truncations of the Ixolaris protein preferably exhibit binding affinity for Factor Xa, X, or VIIa, with the resulting biological effect of Factor Xa, X, or VIIa binding, anticoagulant activity, generation of antibodies that specifically bind Ixolaris, or identification of compounds that can be used to modulate coagulation function.

Functional equivalents of Ixolaris include those naturally occurring and engineered, as judged by any of a number of criteria, including, but not limited to, the binding affinity for Factor Xa, X, or VIIa, the resulting biological effect of factor Xa, X, or VIIa binding, anticoagulant activity, generation of antibodies that specifically bind Ixolaris, and identification of compounds that can be used to in the methods of the present invention.

Truncations of Ixolaris preferably comprise an active fragment of an Ixolaris polypeptide.

In addition to the Ixolaris nucleotide sequences described above, full or partial length Ixolaris cDNA present in the same species and/or homologs of the Ixolaris gene present in other species can be identified and readily isolated, without undue experimentation, by molecular biological techniques well known in the art. For example, expression libraries of cDNAs synthesized from salivary gland mRNA derived from the organism of interest can be screened using labeled Factor Xa, X, or VIIa derived from that species, e.g., a Factor Xa, X, or VIIa fusion protein. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the Ixolaris gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15-30 base pairs of the Ixolaris nucleotide sequence, SEQ ID NO: 3. The hybridization washing conditions used should be of a lower stringency when the cDNA library is derived from an organism different from the type of organism from which the labeled sequence was derived. With respect to the cloning of a human Ixolaris homolog, using tick Ixolaris probes, for example, hybridization can, for example, be performed at 65 C overnight in Church's buffer (7% SDS, 250 mM *NaHPO*4, 2 μM EDTA, 1% BSA). Washes can be done with 2 times SSC, 0.1% SDS at 65 C. and then at 0.1 times SSC, 0.1% SDS at 65 C.

Low stringency conditions are well known to those of skill in the art, and will vary predictably depending on the specific organisms from which the library and the labeled sequences are derived. For guidance regarding these and other hybridization conditions see, for example, Sambrook et al. 1989 Molecular Cloning, A Laboratory Manual, Cold Springs Harbor Press, N.Y.; Ausubel et al. 1989 Current Protocols in Molecular Biology, Green Publishing Associates and Wiley Interscience, N.Y.

Alternatively, the labeled Ixolaris nucleotide probe may be used to screen a genomic library derived from the organism of interest, again, using appropriately stringent conditions.

Further, a full or partial length Ixolaris cDNA present in the same species and/or homologs of the Ixolaris gene present in other species may be isolated from nucleic acid of the organism of interest by performing PCR using two degenerate oligonucleotide primer pools designed on the basis of amino acid sequences within the Ixolaris gene product disclosed herein. The template for the reaction may be cDNA obtained by reverse transcription of mRNA prepared from, for example, cell lines or tissue, such as salivary gland, known or suspected to express an Ixolaris gene allele.

The PCR product may be subcloned and sequenced to ensure that the amplified sequences represent the sequences of an Ixolaris gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the Ixolaris gene, such as, for example, salivary gland). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al. 1989, supra.

In certain preferred embodiments, an active fragment of an Ixolaris polypeptide comprises at least 40 contiguous amino acids or more, 50 contiguous amino acids or more, 60 contiguous amino acids or more, 70 contiguous amino acids or more, 80 contiguous amino acids or more, 90 contiguous amino acids or more, 100 contiguous amino acids or more, 110 contiguous amino acids or more, 120 contiguous amino acids or more, 130 contiguous amino acids or more, 140 contiguous amino acids or more, 150 contiguous amino acids or more, 160 contiguous amino acids or more, or the full length sequence of the amino acid sequence corresponding to SEQ ID NO: 2.

In other embodiments, an active Ixolaris polypeptide comprises at least 80% overall identity or more, 85% overall identity or more, 90% overall identity or more, 95% overall identity or more to a fragment of at least 50 contiguous amino acids of SEQ ID NO: 2.

The invention encompasses nucleotide sequences that encode not only Ixolaris but also its functional domains, besides truncations thereof, as well as substitutions, insertions, and deletions (including fusion proteins) thereof. These include, but are not limited to nucleotide sequences encoding a Kunitz domain of the Ixolaris protein. It is believed that a Kunitz domain may be responsible for the observed anticoagulant activity. Certain representative Kunitz domains include between amino acids 18 and 68 (first Kunitz domain) and its amino and carboxy truncations.

Amino acid substitutions may be of a conserved or non-conserved nature. Conserved amino acid substitutions consist of replacing one or more amino acids of the Ixolaris or Ixolaris-related sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the Ixolaris or Ixolaris-related sequence with amino acids possessing dissimilar charge, size, and/or hydrophobicity characteristics, such as, for example, a glutamic acid (E) to valine (V) substitution. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. One or more such substitutions may be introduced into the Ixolaris or Ixolaris-related sequence, as long as such substitutions result in variants which exhibit binding affinity for Factor Xa, X, or VIIa, the resulting biological effect of Factor Xa, X, or VIIa binding, anticoagulant activity, generation of antibodies that specifically bind Ixolaris, or identification of compounds that can be used to modulate coagulation function.

Amino acid insertions may consist of single amino acid residues or stretches of residues. The insertions may be made at the carboxy or amino terminal end of the Ixolaris or Ixolaris-related sequence, as well as at a position internal to the sequence. Such insertions made at either the carboxy or amino terminus of the sequence of interest may be of a broader size range. One or more such insertions may be introduced into the Ixolaris or Ixolaris-related sequence, as long as such insertions result in variants which exhibit binding affinity for Factor Xa, X, or VIIa, the resulting biological effect of Factor Xa, X, or VIIa binding, anticoagulant activity, generation of antibodies that specifically bind Ixolaris, or identification of compounds that can be used to modulate coagulation function.

Deletions of Ixolaris or Ixolaris-related sequences are also within the scope of the invention. Such deletions consist of the removal of one or more amino acids from the Ixolaris or Ixolaris-related sequence. Such deletions may involve a single contiguous or greater than one discrete portion of the original sequences. One or more such deletions may be introduced into the Ixolaris or Ixolaris-related sequence, as long as such deletions result in variants which exhibit binding affinity for Factor Xa, X, or VIIa, the resulting biological effect of Factor Xa, X, or VIIa binding, anticoagulant activity, generation of antibodies that specifically bind Ixolaris, or identification of compounds that can be used to modulate coagulation function.

The preferred amino acid sequences of the present invention are isolated from their natural source by any of the methods known in the art. These methods include preparing a soluble extract and enriching the extract using chromatographic methods on different solid support matrices.

The preferred isolated Ixolaris and Ixolaris-related amino acid sequences of the present invention may be synthesized by standard methods known in the chemical arts.

The isolated amino acid sequences of the present invention may be prepared using solid-phase synthesis, such as that described by Merrifield, 1964 J Amer Chem Soc 85:2149 or other equivalent methods known in the chemical arts, such as the method described by Houghten 1985 PNAS USA 82:5132 (1985).

Alternatively, the preferred isolated Ixolaris and Ixolaris-related amino acid sequences of the present invention may be made by recombinant DNA methods taught herein and well known in the biological arts (Sambrook et al. 1989 Molecular Cloning, A Laboratory Manual, Cold Springs Harbor Press, N.Y.; Ausubel et al. 1989 Current Protocols in Molecular Biology, Green Publishing Associates and Wiley Interscience, N.Y.). Such methods can be used to construct expression vectors containing the cDNA and other nucleotide sequences described in the section above and appropriate transcriptional and translational control signals. These methods include, for example, in vitro recombinant DNA techniques, synthetic techniques, and in vivo genetic recombination.

Methods

Provided in certain aspects are methods of inhibiting growth of a cell expressing tissue factor (TF), comprising contacting the cell with an effective amount of a tissue factor pathway inhibitor (TFPI) compound, such that the growth of the cell is inhibited.

Also provided in other aspects are methods of treating or preventing a TF mediated or associated disease or process in a subject, comprising administering to the subject a TFPI compound in an amount effective to treat or prevent the TF mediated or associated disease or process.

Provided in other certain aspects are methods of treating or preventing the growth or metastasis of tumor cells in a subject, comprising administering to the subject a TFPI compound in an amount effective to treat or prevent the growth or metastasis of the tumor cells.

In certain preferred embodiments, the TFPI compound comprises a tick saliva protein.

Preferably, the TFPI compound comprises at least an active fragment of an Ixolaris polypeptide.

The present invention contemplates treating or preventing a TF mediated or associated disease or process in a subject.

In preferred embodiments, the disease is a vascular disease.

Accordingly, the invention features a method of treating or preventing a vascular disease in a subject comprising administering to the subject a TFPI compound in an amount effective to treat or prevent the vascular disease.

Vascular disease includes any disease or disorder that affects the circulatory system, and can be a disease of the arteries, veins and lymph vessels to blood disorders that affect circulation. Examples of vascular diseases include, but are not limited to, Peripheral Artery Disease (PAD), diabetic retinopathy, age-related macular degeneration, aneurysm, renal artery disease, Raynaud's Phenomenon (also called Raynaud's Disease or Raynaud's Syndrome), Buerger's Disease, Peripheral Venous Disease, Varicose Veins, Venous Blood Clots, Deep vein thrombosis.

In certain preferred embodiments, the disease is cancer.

The cancer to be treated according to the present invention can be a solid tumor or a non-solid tumor (e.g., blood tumors such as leukemias).

The cancer can be metastatic.

Cancer can occur in nearly any tissue of the body including, but not limited to, adrenocortical carcinoma, anal cancer, bladder cancer, brain stem glioma, brain tumors, breast cancer, cerebellar astrocytoma/malignant glioma, cervical cancer, chronic myeloproliferative disorders, colon cancer, endometrial cancer, ependymoma, esophageal cancer, Ewing family of tumors, extracranial germ cell tumors, extragonadal germ cell tumors, extrahepatic bile duct cancer, gallbladder cancer, gastric cancer, gastrointestinal carcinoid tumors, gestational trophoblastic tumors, hypopharyngeal cancer, islet cell carcinoma (Endocrine Pancreas), islet cell tumors (endocrine pancreas), laryngeal cancer, leukemia, acute lymphoblastic; leukemia, acute myeloid; leukemia, chronic lymphocytic; leukemia, chronic Myelogenous, lip and oral cavity cancer, liver cancer, lung cancer, non-small cell; lung cancer, small cell, lymphoma, Hodgkin's, lymphoma, Non-Hodgkin's, lymphoma, AIDS-Related, lymphoma, lymphoma, primary CNS, melanoma, intraocular (Eye), medulloblastoma, Merkel cell carcinoma, mesothelioma, mycosis fungoides and the Sézary Syndrome, myelodysplastic and myeloproliferative diseases, myelodysplastic Syndromes, myeloid leukemia/other myeloid cancers, nasopharyngeal cancer, neuroblastoma, oropharyngeal cancer, osteosarcoma/malignant fibrous histiocytoma of bone, ovarian epithelial cancer, ovarian germ cell tumors, pancreatic cancer, paranasal sinus and nasal cavity cancer, parathyroid cancer, penile cancer, pheochromocytoma, pituitary tumors, prostate cancer, rectal cancer, renal cell cancer, retinoblastoma, rhabdomyosarcoma, salivary gland cancer, sarcoma, soft Tissue, sarcoma, Kaposi, skin cancer, small Intestine cancer, squamous neck cancer with occult primary, supratentorial primitive neuroectodermal tumors and pineoblastoma, testicular cancer, thymoma and thymic carcinoma, thyroid cancer, transitional cell cancer of the renal pelvis and ureter, urethral cancer, uterine sarcoma, vaginal cancer, visual pathway and hypothalamic glioma, and vulvar cancer.

Preferably, the cancer comprises a tumor with high expression or production of one or more proteins selected from the group consisting of tissue factor (TF), Factor VIIa, Factor Xa, thrombin, vascular endothelial growth factor (VEGF), interleukin-8 (IL-8), one or more matrix metalloproteases, Factor VII, and Factor X, as compared to a control cell not derived from the tumor.

In further embodiments, the cancer comprises a tumor wherein the tumor expresses TF around the necrotic core.

In other further embodiments, the tumor is a highly vascularized tumor.

In preferred embodiments, the tumor comprises a central nervous system tumor. Astrocytomas and oligodendrogliomas are the most common primary tumors of the adult brain. Both tumors are types of gliomas. Primary brain tumors arise from cells of the brain itself rather than traveling, or metastasizing, to the brain from another location in the body. Gliomas can be slowly growing (low-grade, grades 1 and 2), or rapidly growing (high-grade, grades 3 and 4).

In preferred embodiments, the central nervous system tumor is a glioblastoma.

Glioblastoma multiforme is the most aggressive of the gliomas, a collection of tumors arising from glia or their precursors within the central nervous system. Clinically, gliomas are divided into four grades; unfortunately, the most aggressive of these, grade 4 or glioblastoma multiforme (GBM), is also the most common in humans. Most patients with GBMs die of their disease in less than a year and essentially none has long-term survival.

In other certain preferred embodiments, the tumor comprises a squamous cell tumor, for example a melanoma. Melanoma, the most serious type of skin cancer, develops in the cells that produce melanin, the pigment that gives your skin its color. Melanoma can also form in the eyes and, more rarely, in internal organs, such as your intestines. Skin cancer is the most common cancer in the United States, and continues to rapidly increase. Although other forms of skin cancer, such as basal cell and squamous cell carcinomas, are on the rise, the greatest increase has been in melanoma. Most melanomas appear without any accompanying symptoms. Approximately 70 percent of these cancers arise from normal-appearing skin, while the remaining 30 percent arise from an existing mole. If left untreated, the tumor can spread downward into deeper skin layers, and to lymph nodes and internal organs.

Methods of the present invention encompass treating or preventing the growth of tumor cells. Preferably, in certain embodiments, treating or preventing the growth of tumor cells comprises at least one selected from the group consisting of decreasing the rate of tumor growth, stopping tumor growth, shrinking the tumor, lessening tumor burden, preventing metastasis, or reducing at least one sign or symptom associated with the presence of a tumor.

In related embodiments, one or more tumor markers are a sign or symptom associated with the presence of a tumor.

As described herein, in the methods of the present invention, the TFPI compound comprises a tick saliva protein. In further preferred embodiments, the TFPI compound comprises at least an active fragment of an Ixolaris polypeptide.

In certain methods of the invention, administering a tick saliva protein inhibits angiogenesis in the subject.

Angiogenesis is meant to refer to the process of forming new blood vessels in a subject.

Angiogenesis is involved in many diseases. For example, cardiovascular diseases such as angioma, angiofibroma, vascular deformity, atherosclerosis, synechia and edemic sclerosis; and opthalmological diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis are related to angiogenesis. Chronic inflammatory diseases such as arthritis; dermatological diseases such as psoriasis, telangiectasis, pyogenic granuloma, seborrheic dermatitis, venous ulcers, acne, rosacea (acne rosacea or erythematosa), warts (verrucas), eczema, hemangiomas, lymphangiogenesis are also angiogenesis-dependent.

Tumor angiogenesis is the proliferation of a network of blood vessels that penetrates into cancerous growths, supplying nutrients and oxygen and removing waste products. The FDA has approved bevacizumab for use with other drugs to treat colorectal cancer that has spread to other parts of the body, some non-small cell lung cancers, and some breast cancers that have spread to other parts of the body. Bevacizumab was the first angiogenesis inhibitor proven to delay tumor growth and, more importantly, extend the lives of patients. The FDA has also approved other drugs with anti-angiogenic activity as cancer therapies for multiple myeloma, mantle cell lymphoma, gastrointestinal stromal tumors (GIST), and kidney cancer. In certain embodiments of the present invention, and anti-angiogenesis agent is administered with a TFPI.

In any of the methods described herein, the method may further comprise identifying a subject in need of treatment with a TFPI compound.

In any of the methods described herein, the method may further comprise monitoring a subject for effects of treatment with TFPI compound.

Assessment of the efficacy of a TFPI compound can be determined by monitoring the subject for amelioration of at least one sign or symptom of cancer.

In certain preferred embodiments, the present invention further comprises monitoring the subject for amelioration of at least one sign or symptom of cancer.

The TFPI compounds of the present invention can be administered alone, or can be administered in combination concurrently or sequentially with another agent. For example, the TFPI compounds of the present invention are used alone, in combination with other compounds of the present invention, or in combination with one or more other agents, for example, but not limited to, a cytotoxic agent, an anti-neoplastic agent, an immunosuppressive, and a VEGF antagonist.

For example, the TFPI compounds may be administered with an anti-neoplastic agent, for example, but not necessarily limited to acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate;

trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elformithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin and monoclonal antibodies such as rituximab, trastuzumab and cetuximab.

Pharmaceutical compositions comprising the TFPI compounds of the present invention are administered in vivo, ordinarily in a mammal, preferably in a human. In employing them in vivo, the pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixirs taken on a daily basis.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

After pharmaceutical compositions have been prepared, they can be placed in an appropriate container and labeled for treatment of an indicated condition.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of cell lines, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example TFPI compound, preferably a tick saliva protein, preferably an active fragment of Ixolaris polypeptide, which ameliorates the symptoms or conditions. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, $LD_{50}/dED_{50}$. Pharmaceutical compositions which exhibit large therapeutic indices are preferred. The data obtained from cell culture assays and animal studies are used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The compositions preferably contain from about 0.01 to 99 weight percent, more preferably from about 2 to 60 percent, of therapeutic agent together with the adjuvants, carriers and/or excipients. Preferably, the amount of active compound in such therapeutically useful compositions is such that a suitable dosage unit will be obtained. Preferred compositions according to the present invention are prepared so that the active fragment of the Ixolaris polypeptide is administered at a daily dose of about 1 μg/kg to about 1000 μg/kg, about 10 μg/kg to about 500 μg/kg, about 10 μg/kg to about 750 μg/kg, about 25 μg/kg to about 1000 μg/kg, about 50 μg/kg to about 1000 μg/kg, about 50 μg/kg to about 500 μg/kg, about 25 μg/kg to about 500 μg/kg, or about 25 μg/kg to about 250 μg/kg.

The administration of the TFPI compound can be carried out as frequently as required and for a duration that is suitable to provide its effects, e.g. effective treatment for cancer or a vascular disease, or its underlying pathological conditions.

For example, administration of the therapeutic agent can be carried out with a single sustained-release dosage formulation or with multiple daily doses of the therapeutic agent. The amount to be administered will, of course, vary depending upon the treatment regimen.

In certain preferred embodiments, the active fragment of the Ixolaris polypeptide is administered one time or more, two times or more, three times or more, four times or more, five times or more, six times or more, seven times or more, eight times or more, ten times or more, fifteen times or more, twenty times or more, or twenty five times or more.

The mammal to be treated in accordance with the present invention can be a rodent, dog, cat, cow, horse, sheep, pig, llama, alpaca, non-human primate. Preferably the mammal to be treated is a human.

Gene Therapy

In addition to the administration of therapeutic agents, various gene therapy approaches are contemplated for the methods of the invention, e.g. methods of treating or preventing TF mediated or associated diseases or processes, e.g. cancer or a vascular disease, as described above. In the various gene therapy approaches, a genetic construct is utilized for transformation of cells, preferably patient cells, either in vivo or ex vivo. In the latter case the cells are collected from the patient to be treated, transformed, and then reintroduced into the patient.

Gene therapy approaches for treating these conditions utilize an expression vector or plasmid that contains therein a recombinant gene (or genetic construct) encoding a therapeutic protein or nucleic acid. Exemplary therapeutic proteins encoded by the recombinant gene include, without limitation, Ixolaris (Genbank Accession AF286029, which is hereby incorporated by reference in its entirety) and Ixolaris-2 (Genbank Accession AY674279, which is hereby incorporated by reference in its entirety), or, for example, a tissue factor pathway inhibitor (TFPI, Genbank Accessions NM 006287 (TFPI var. 1), NM 001032281 (TFPI, var. 2).

The recombinant gene includes, operatively coupled to one another, an upstream promoter operable in mammalian cells and optionally other suitable regulatory elements (i.e., enhancer or inducer elements), a coding sequence that encodes the therapeutic protein or nucleic acid (described above), and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in preferred cell types, for example in vascular smooth muscle cells, such as SM22 (Ribault et al., "Chimeric Smooth Muscle-Specific Enhancer/Promoters: Valuable Tools for Adenovirus-mediated Cardiovascular Gene Therapy," Circulation Res. 88(5): 468-475 (2001), which is hereby incorporated by reference in its entirety). Tissue specific promoters can also be made inducible/repressible using, e.g., a TetO response element. Known recombinant techniques can be utilized to prepare the recombinant gene, transfer it into the expression vector, and administer the vector to a patient. Exemplary procedures are described in Sambrook et al., Molecular Cloning: A Laboratory Manual, Second Edition, Cold Spring Harbor Press, N.Y. (1989), which is hereby incorporated by reference in its entirety. One of skill in the art can readily modify these procedures, as desired, using known variations of the procedures described therein.

The recombinant gene can be delivered into targeted cells (to be transformed) as either naked DNA that can be taken up by the cell, or by using a viral (infective) vector or a non-infective delivery vehicle.

Any suitable viral or infective transformation vector can be used. Exemplary viral vectors include, without limitation, adenovirus, adeno-associated virus, retroviral vectors, Adenovirus gene delivery vehicles can be readily prepared and utilized given the disclosure provided in Berkner, Biotechniques 6:616-627 (1988) and Rosenfeld et al., Science 252:431-434 (1991), WO 93/07283, WO 93/06223, and WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired protein or polypeptide or nucleic acid. The use of adeno-associated viral gene delivery vehicles in vitro is described in Chatterjee et al., Science 258:1485-1488 (1992); Walsh et al., Proc. Nat'l Acad. Sci. USA 89:7257-7261 (1992); Walsh et al., J. Clin. Invest. 94:1440-1448 (1994); Flotte et al., J. Biol. Chem. 268:3781-3790 (1993); Ponnazhagan et al., J. Exp. Med. 179:733-738 (1994); Miller et al., Proc. Nat'l Acad. Sci. USA 91:10183-10187 (1994); Einerhand et al., Gene Ther. 2:336-343 (1995); Luo et al., Exp. Hematol. 23:1261-1267 (1995); and Zhou et al., Gene Ther. 3:223-229 (1996), each of which is hereby incorporated by reference in its entirety. In vivo use of these vehicles is described in Flotte et al., Proc. Nat'l Acad. Sci. USA 90:10613-10617 (1993); and Kaplitt et al., Nature Genet. 8:148-153 (1994), each of which is hereby incorporated by reference in its entirety.

Retroviral vectors which have been modified to form infective transformation systems can also be used to deliver a recombinant gene encoding a desired protein or polypeptide or nucleic acid product into a target cell. One such type of retroviral vector is disclosed in U.S. Pat. No. 5,849,586 to Kriegler et al., which is hereby incorporated by reference in its entirety.

Alternatively, a number of non-infective delivery vehicles are available for delivering the genetic construct in vivo or ex vivo. A colloidal dispersion system can be used to deliver the genetic construct to a patient. Colloidal dispersion systems include macromolecule complexes, nanocapsules, microspheres, beads, and lipid-based systems including oil-in-water emulsions, micelles, mixed micelles, and liposomes. The preferred colloidal system of this invention is a lipid preparation including uni-lamellar and multi-lamellar liposomes.

Liposomes are artificial membrane vesicles that are useful as delivery vehicles in vitro and in vivo. It has been shown that large uni-lamellar vesicles (LUV), which range in size from about 0.2 to about 4.0 .mu.m, can encapsulate a substantial percentage of an aqueous buffer containing DNA molecules (Fraley et al., Trends Biochem. Sci. 6:77 (1981), which is hereby incorporated by reference in its entirety). In addition to mammalian cells, liposomes have been used for delivery of polynucleotides in yeast and bacterial cells. For a liposome to be an efficient transfer vehicle, the following characteristics should be present: (1) encapsulation of the DNA molecules at high efficiency while not compromising their biological activity; (2) substantial binding to host organism cells; (3)

delivery of the aqueous contents of the vesicle to the cell cytoplasm at high efficiency; and (4) accurate and effective expression of genetic information (Mannino et al., Biotechniques 6:682 (1988), which is hereby incorporated by reference in its entirety). In addition to such LUV structures, multilamellar and small unilamellar lipid preparations which incorporate various cationic lipid amphiphiles can also be mixed with anionic DNA molecules to form liposomes (Felgner et al., Proc. Natl. Acad. Sci. USA 84(21): 7413 (1987), which is hereby incorporated by reference in its entirety).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and typically the presence of divalent cations. The appropriate composition and preparation of cationic lipid amphiphile:DNA formulations are known to those skilled in the art, and a number of references which provide this information are available (e.g., Bennett et al., J. Liposoine Research 6(3):545 (1996), which is hereby incorporated by reference in its entirety).

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. Examples of cationic amphiphilic lipids useful in formulation of nucleolipid particles for polynucleotide delivery include the monovalent lipids N-[1-(2,3-dioleoyloxy)propyl]-N,N,N,-trimethyl ammonium methyl-sulfate, N-[2,3-dioleoyloxy)propyl]-N,N,N-trimethyl ammonium chloride, and DC-cholesterol, the polyvalent lipids LipofectAMINE, dioctadecylamidoglycyl spermine, TRANSFECTAM, and other amphiphilic polyamines. These agents may be prepared with helper lipids such as dioleoyl phosphatidyl ethanolamine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization. The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

A further alternative for delivery of DNA is the use of a polymeric matrix which can provide either rapid or sustained release of the genetic construct to the organism. A number of polymeric matrices are known in the art and can be optimized with no more than routine skill.

The genetic constructs can be used either for direct administration to a patient, in which patient cell transformation occurs in vivo, or for ex vivo transformation of previously harvested patient cells that can then be reintroduced into the patient to be treated.

Preferred routes for administering a genetic construct for in vivo transformation include (i) administering the genetic construct (as either an infective vector or as a component within a delivery vehicle) into the right ventricle or a peripheral vein of the patient, and (ii) administering the genetic construct (as a component of a delivery vehicle) via inhalation. Either of these routes will effectively cause the genetic construct to be delivered into small arterial vessels of lung tissue.

When using ex vivo transformation, it is preferable to harvest progenitor stem cells from the patient, including progenitor endothelial cells or progenitor vascular smooth muscle cells. After harvesting (and optionally purifying the population of cells), the harvested progenitor cells are transformed, transformants are selected, and then the transformed progenitor cells are reintroduced into the lung tissue of the patient. Reintroduction of the transformed cells is preferably carried out by right ventricular administration or peripheral intravenous administration. The ex vivo transformation of endothelial progenitor cells is described in Zhao et al., "Rescue of Monocrotaline-Induced Pulmonary Arterial Hypertension Using Bone Marrow-Derived Endothelial-Like Progenitor Cells: Efficacy of Combined Cell and eNOS Gene Therapy in Established Disease," Circ. Res. 96(4):442-450 (2005), which is hereby incorporated by reference in its entirety).

Antibodies to Ixolaris Proteins

Antibodies that specifically recognize one or more epitopes of Ixolaris, or active fragments thereof, or epitopes of conserved variants of Ixolaris, or peptide fragments of Ixolaris are also encompassed by the invention. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above.

The antibodies of the invention may be used, for example, for diagnostic purposes and for the identification of concentration levels of Ixolaris in various biological fluids. Immunoassays utilizing these antibodies may be used as a diagnostic test, such as to detect infection of a mammalian host by a tick or to detect Ixolaris from a tick in a tissue of the mammalian host. Also, such immunoassays may be used in the detection and isolation of Ixolaris from tissue homogenates, cloned cells, and the like.

For the production of antibodies, various host animals may be immunized by injection with Ixolaris, an Ixolaris peptide (e.g., one corresponding to a functional domain), truncated Ixolaris proteins, polypeptides, or peptides, functional equivalents of Ixolaris or variants of Ixolaris. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975 Nature 256:495-497; and U.S. Pat. No. 4,376, 110), the human B-cell hybridoma technique (Kosbor et al. 1983 Immunology Today 4:72; Cole et al. 1983 PNAS USA 80:2026-2030), and the EBV-hybridoma technique (Cole et al. 1985 Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al. 1984 PNAS USA 81:6851-6855; Neuberger et al. 1984 Nature 312:604-608; Takeda et al. 1985 Nature 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Figure 2D:
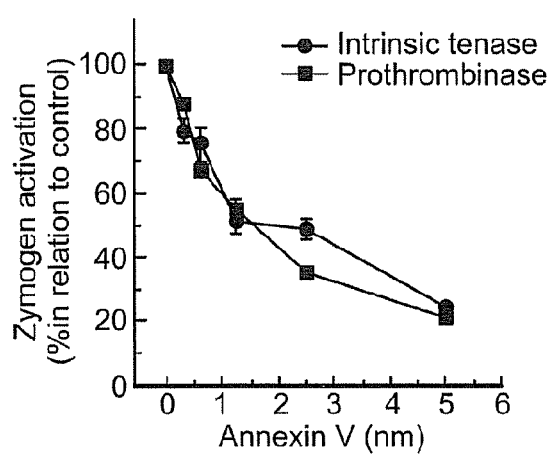

Alternatively, techniques described for the production of single chain antibodies (U.S. Pat. No. 4,946,778; Bird 1988 Science 242:423-426; Huston et al. 1988 PNAS USA 85:5879-5883; and Ward et al. 1989 Nature 334:544-546) can be adapted to produce single chain antibodies against Ixolaris gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse et al. 1989 Science 246:1275-1281) to allow rapid and easy identification of monoclonal Fab fragments with the desired specificity.

Antibodies to Ixolaris can, in turn, be utilized to generate anti-idiotype antibodies that "mimic" Ixolaris, using techniques well known to those skilled in the art. (See, e.g., Greenspan & Bona 1993 FASEB J 7(5):437-444; and Nissinoff 1991 J Immunol 147(8):2429-2438). For example antibodies which bind to a Kunitz domain and competitively inhibit the binding of Factor Xa, X, or VIIa to Ixolaris can be used to generate anti-idiotypes that "mimic" the Kunitz domain and, therefore, bind and neutralize Ixolaris. Such neutralizing anti-idiotypes or Fab fragments of such anti-idiotypes can be used in regimens to neutralize Ixolaris.

Kits

The present invention also features kits for practicing any one of the methods as described herein, e.g. treating or preventing a TF mediated or associated disease or process in a subject or treating or preventing the growth or metastasis of tumor cells in a subject, and instructions for use.

Preferably, the kits of the present invention comprise a TFPI compound, preferably a tick saliva protein.

In preferred embodiments, the TFPI compound comprises at least an active fragment of an Ixolaris polypeptide.

Kits of the invention may also contain a pharmaceutically acceptable carrier, a physiologically acceptable carrier, instructions for use, a contain, a vessel for administration, an assay substrate, or any combination thereof.

EXAMPLES

It should be appreciated that the invention should not be construed to be limited to the examples that are now described; rather, the invention should be construed to include any and all applications provided herein and all equivalent variations within the skill of the ordinary artisan.

Example 1

Functional TF expressed by U87-MG cells is inhibited by Ixolaris

Previous studies employing the U87-MG human glioma cell line have demonstrated constitutive expression of the clotting initiator protein tissue factor (TF) [20,33]. Accordingly, FIG. 1(A, left) demonstrates positive staining for TF on U87-MG cells, as assessed by flow-cytometric analysis. In fact, comparison with the human breast cancer cell line MDA-MB-231 (FIG. 1A, right) showed that U87-MG express moderate levels of TF. Further enzymatic assays showed that the TF expressed on U87-MG cells is functional. FIG. 1(B) shows that FXa formation was both cell- and FVIIa-dependent, indicating the formation of the FVIIa/TF complex (extrinsic tenase complex).

Ixolaris is a potent inhibitor of the FVIIa/TF complex that blocks FXa formation by forming a quaternary FVIIa/TF/FX/Ixolaris complex in which the FVIIa catalytic site is inactivated [24]. Therefore, it was next determined whether Ixolaris inhibits the extrinsic tenase complex assembled on U87-MG cells. As shown in FIG. 1(C), Ixolaris efficiently decreased FXa formation in this cell-based system.

Example 2

Ixolaris Inhibits PS-Dependent Procoagulant Complexes Assembled on U87-MG Cells Previous studies demonstrate that viable tumor cells may expose the anionic phospholipid phosphatidylserine (PS) at the outer leaflet of the cell membrane [31,34]. This ability allows an alternative pathway for activation of FX through assembly of the intrinsic tenase complex (i.e. FIXa, FVIIIa and PS containing membranes). The presence of PS on the surface of U87-MG cells was demonstrated by flow cytometric assays using annexin-V-FITC (FIG. 2A) and specific anti-PS antibodies (data not shown). This indicates that U87-MG cells normally expose PS on their surface. The ability of tumor cells to promote FX activation through assembly of the intrinsic tenase complex was further investigated. FIG. 2(B) shows that zymogen activation was both cell- and FVIIIa-dependent. Thus, U87-MG glioma cells support the formation of the intrinsic tenase complex.

Assembly of the prothrombinase complex on tumor cells is also supported by PS exposure [31,35]. Accordingly, FIG. 2(C) shows that U87-MG cells potentiate prothrombin activation in the presence of FXa and FVa, its protein cofactor. On the other hand, no thrombin formation has been observed in the absence of cells or in the absence of FVa. These data are consistent with the assembly of the prothrombinase complex on U87-MG cells. The contribution of tumor cell PS to either FXa or thrombin formation was reinforced by the observation that increasing annexin V concentrations progressively decreased zymogen conversion by their respective U87-MG-assembled activating complexes (FIG. 2D).

Figure 2E:
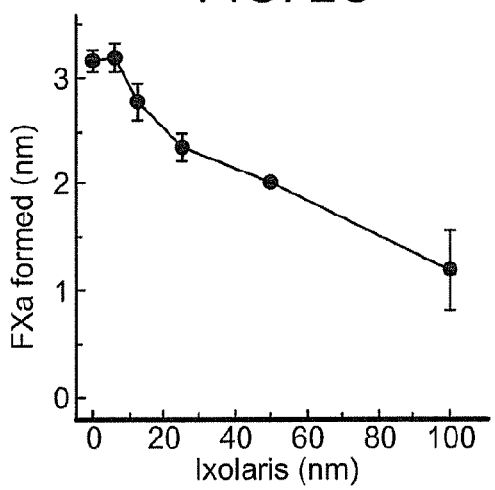
Figure 2F:
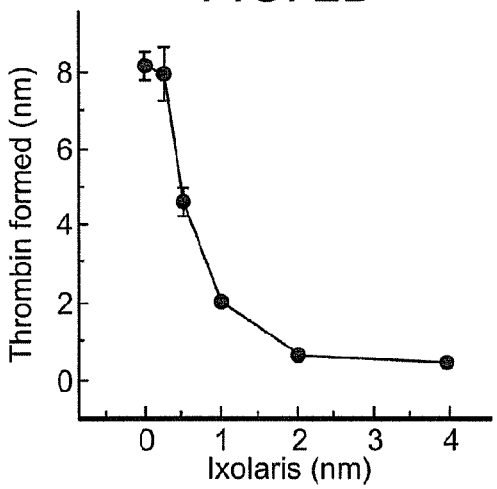

It has been demonstrated that binding of Ixolaris to FX decreases the zymogen recognition by the intrinsic tenase complex, as demonstrated in a purified system [27]. Similarly, increasing Ixolaris concentrations reduced FXa formation by the U87-MG-assembled intrinsic complex (FIG. 2E). Remarkably, effective Ixolaris concentrations in this assay are correlated with zymogen concentration and are expected to be much higher than that required to inhibit the FVIIa/TF complex. Binding of Ixolaris to FXa occurs through a specific heparin binding region in the enzyme that is crucial for prothrombinase complex activity [26]. Therefore, Ixolaris progressively decreased thrombin formation by the U87-MG-assembled prothrombinase complex, as observed in FIG. 2F.

Example 3

Procoagulant Activity of U87-MG Cells is Reversed by Ixolaris

Figure 3A:
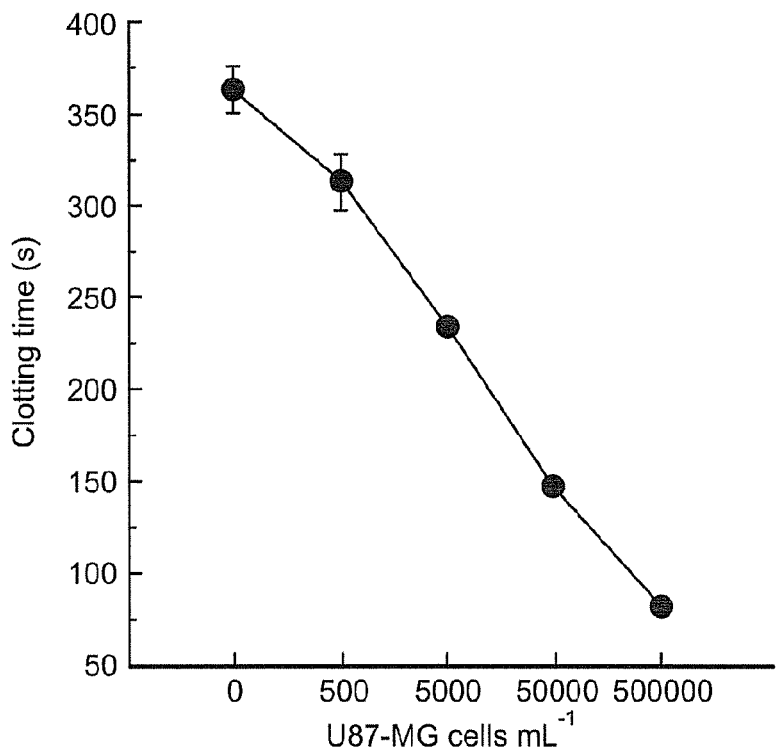
FIGS. 3(A and B) shows procoagulant activity of U87-MG cells is reversed by Ixolaris. (A) U87-MG cells (in PBS) at the indicated concentrations were incubated with human plasma followed by recalcification with 12.5 mM CaCl$_2$. Each point represents mean±SD of three assays. (B) Human plasma was incubated for 5 min with the indicated concentrations of DEGR-FVIIa (FVIIai, grey bars) or Ixolaris (black bars) prior to addition of U87-MG cells (5×10$^5$ cells) followed by recalcification with 12.5 mM CaCl$_2$. Each point represents mean±SD of three assays.
Figure 3B:
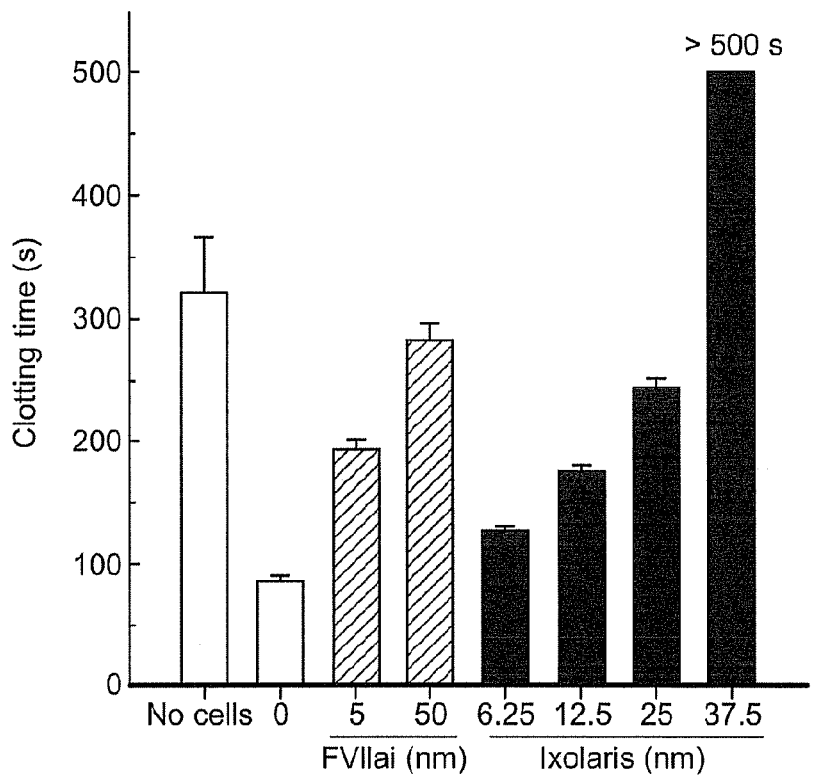

Because U87-MG cells contain the main components to initiate (TF) and to propagate (a PS-containing membrane) blood clotting in a highly efficient manner, the effect of these cells on human plasma clotting was further tested. As shown in FIG. 3(A), increasing cell concentrations considerably accelerates the coagulation time, demonstrating that these cells display potent procoagulant activity. However, TF seems to be important, if not critical, for this ability, because DEGR-FVIIa, which acts as a specific TF/FVIIa inhibitor, completely reversed U87 procoagulant activity (FIG. 3B, grey bars). The ability of Ixolaris to inhibit the tumor-dependent procoagulant activity was further examined. As expected, Ixolaris efficiently reversed tumor-induced plasma coagulation (FIG. 3B, black bars).

Example 4

Ixolaris Inhibits In Vivo Primary Tumor Growth in a Xenograft Model

Figure 4A:
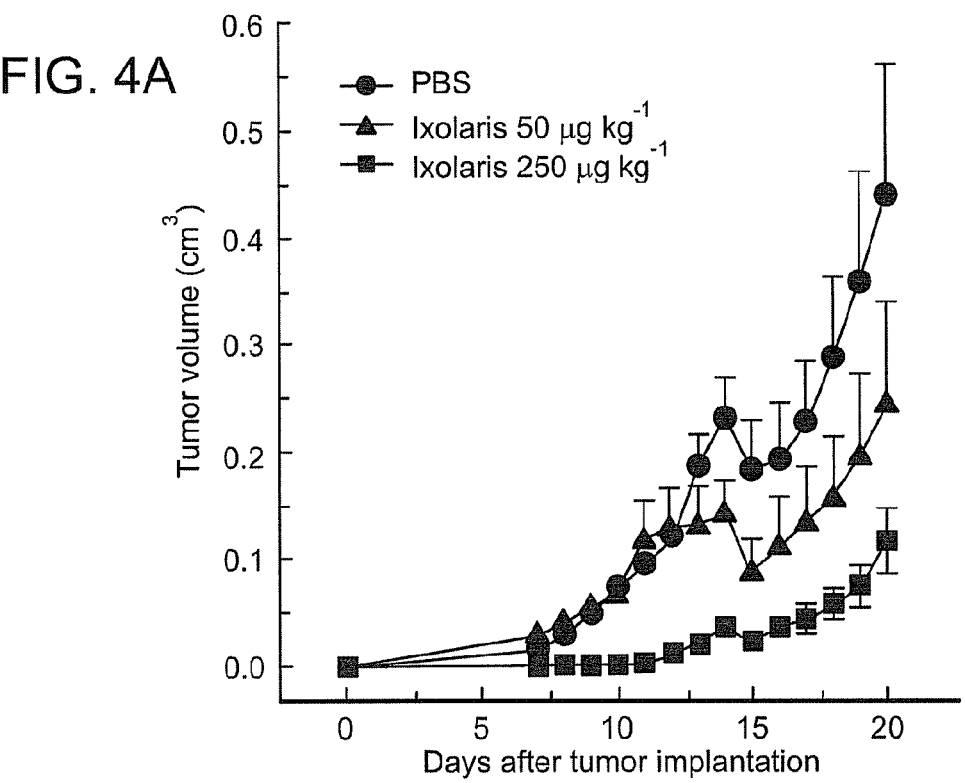
FIGS. 4(A and B) shows Ixolaris inhibits in vivo primary tumor growth in a xenograft model. U87-MG cells were injected subcutaneously (s.c.) into nude mice. Treatment with Ixolaris was initiated 3 days after tumor cell inoculation; control animals were treated with an equivalent volume of PBS. (A) Tumor size was measured at the indicated days. Each point represents mean±SD. (B) After 20 days of tumor cell inoculation, animals were sacrificed and tumors were removed and weighed.
Figure 4B:
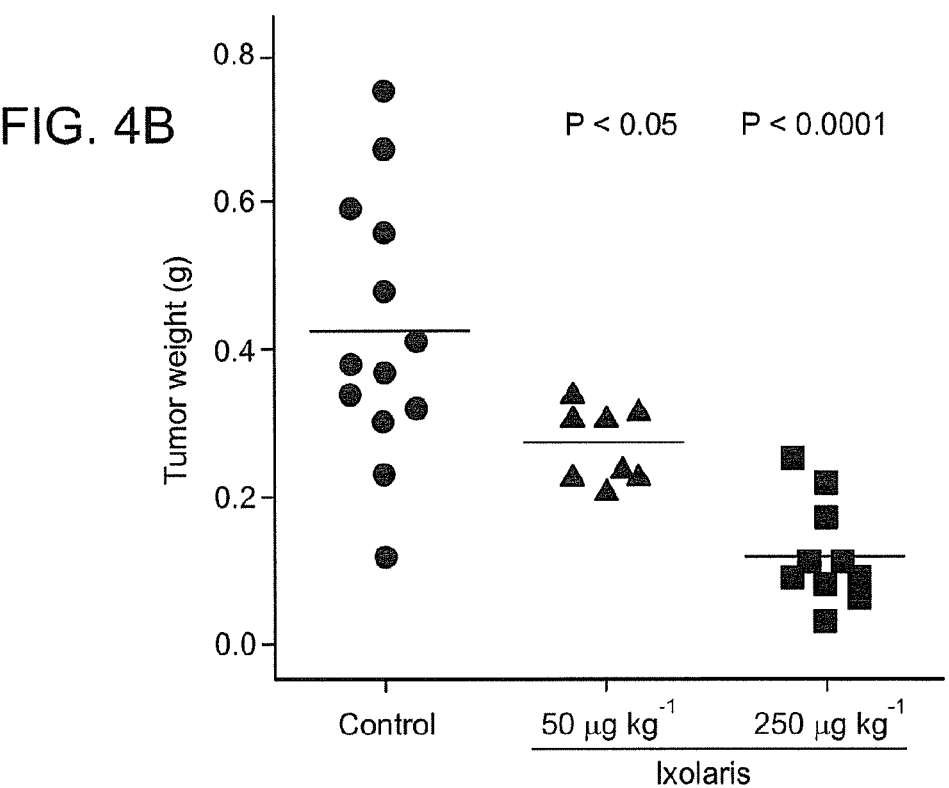

It has been demonstrated that coagulation inhibitors targeting the FVIIa/TF complex reduce primary tumor growth and tumor vessel density [36,37]. In this context, the ability of Ixolaris to interfere with in vivo U87-MG growth was next examined using a xenograft model in nude mice. As may be seen in FIG. 4, treatment with Ixolaris decreased tumor growth progression in a dose-dependent manner (FIG. 4A) with significant reduction in tumor weight in animals treated with either 50 or 250 $\mu g\, kg^{-1}$ (FIG. 4B). In vitro assays for cell proliferation and viability showed no direct toxic effect of Ixolaris on tumor cells (data not shown). In addition, no bleeding has been observed in controls or tumor-bearing animals treated for up to 30 or 20 days, respectively, with both Ixolaris doses (data not shown).

Example 5

Treatment with Ixolaris Decreases Tumor Angiogenesis

Figure 5B:
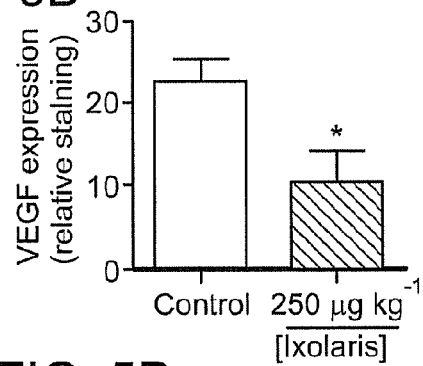
FIG. 5(A-C) shows treatment with Ixolaris decreases tumor angiogenesis. (A) RNA was extracted from tumors obtained from experiments depicted in FIG. 4(B) and further analyzed for VEGF expression using RT-PCR, as described in the Materials and methods section. (B) Bar graph shows decreased VEGF expression in Ixolaris-treated animals (n=5; 10.4±3.6) compared with PBS-treated controls (n=5; 22.7±2.6). VEGF staining (asterisk) and quantification was performed as described in the Materials and methods section. (C) Bar graph shows that there are fewer blood vessels in Ixolaris-treated animals (n=5; 8.9±3.7) than in PBS-treated controls (n=5; 23.9±4.2). Vessel density was evaluated in CD105-stained tumor sections (arrows) as described in the Materials and methods section. Values of P<0.05 were considered to be statistically significant. All values are given as mean±SD.
FIG. 5D is a series of photomicrographs of the immunohistochemical staining that is graphically represented in FIG. 5B and FIG. 5C.
Figure 5C:
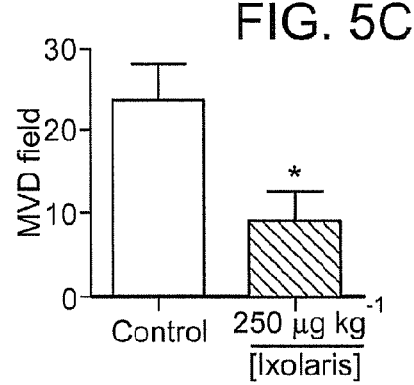

Remarkably, the antitumor effect of Ixolaris was accompanied by a significant decrease in the VEGF mRNA levels within tumors (FIG. 5A). Further immunohistochemistry analysis confirmed that treatment with Ixolaris down regulates VEGF expression (FIG. 5B). Therefore immunohistochemistry analysis also confirmed that treatment with Ixolaris reduces tumor vessel density, as assessed by CD105 staining (FIG. 5C). FIG. 5D is a series of photomicrographs of the immunohistochemical staining that is graphically represented in FIG. 5B and FIG. 5C.

Example 6

Inhibition of TF by Ixolaris Reduces Primary Tumor Growth and Metastasis in a Murine Model of Melanoma Melanoma is a highly metastatic cancer and there is strong evidence that TF activity contributes to its aggressive pattern. In this context, it has been suggested that TF inhibitors may attenuate primary tumor growth and metastasis. In this study we evaluated the effect of Ixolaris, an exogenous TF inhibitor, in a murine model of melanoma employing B16F10 cells. TF expression on B16F10 cells was evaluated by flow-cytometry. TF activity on tumor cells was evaluated by measuring factor X activation by FVIIa. The effects of Ixolaris on primary melanoma growth or metastasis were evaluated by subcutaneous or intravenous injection of B16F10 cells in C57/BL6 mice, respectively. VEGF expression on primary tumors was evaluated by immunohistochemistry. Flow-cytometric analyses showed constitutive TF expression by B16F10 cells. In vitro, murine and human tumor-derived TF activity was blocked equally well by Ixolaris. Intravenous co-inoculation of B16F10 cells and Ixolaris (250 micrograms/kg) dramatically decreased the number of pulmonary tumor nodules (47±10 vs 4±1 in the control group). Further primary growth assays were performed and animals were treated daily with Ixolaris (50 or 250 micrograms/kg, i.p.) from day 3 to 18 after s.c. inoculation of tumor cells. A significant decrease in tumor weight was observed for both Ixolaris doses (28% and 58% respectively) as compared to non-treated animals. In this regard, immunohistochemistry analyses showed that inhibition of melanoma growth by Ixolaris is accompanied by a significant down regulation of VEGF and angiogenesis in the tumor mass.

The data presented herein demonstrate that Ixolaris targets B16F10-derived TF resulting in decreased metastatic potential and reduced primary tumor growth and angiogenesis.

It is hypothesized that targeting the blood clotting cascade represents a feasible therapeutic approach for treatment of glioblastoma [23]. The examples described herein demonstrate for the first time that Ixolaris, a potent exogenous TF inhibitor, blocks the in vivo growth of human glioblastoma (U87-MG) cells in a xenograft model. This phenomenon was accompanied by a significant decrease in VEGF expression as well as diminished tumor angiogenesis.

The data presented herein show that Ixolaris is highly efficient in inhibiting the U87-MG-assembled extrinsic tenase complex. Therefore, the antitumor effect of Ixolaris is likely to be attributable to the suppression of tumor-associated FVIIa/TF complex activity. This is supported by other studies showing that: (i) xenograft models employing a specific anti-human TF showed that suppression of tumor—but not host-derived TF coagulant activity is sufficient to impair primary tumor growth [36,38]; (ii) low-TF mice exhibit unaltered growth of TF-expressing tumor cell lines, as compared with wild-type mice [39]. Most remarkable, tumor progression is also impaired by a TF-directed monoclonal antibody that specifically suppresses PAR-2-mediated signaling in tumor cells without affecting FVIIa/TF complex-mediated coagulation [40]. It has been clearly demonstrated that Ixolaris blocks the FVIIa catalytic site [24] and therefore it possibly suppresses FVIIa/TF complex-mediated signaling in addition to its anti-coagulant unction on tumor cells.

The in vitro data presented herein demonstrates that, in addition to the FVIIa/TF complex, Ixolaris inhibits PS-dependent coagulation complexes assembled on U87-MG cells, through interaction with FX or FXa. Therefore, inhibition of thrombin formation by the prothrombinase might also contribute to the antitumor activity of Ixolaris. In this regard, it has been demonstrated that argatroban, a specific thrombin inhibitor, reduces in vivo growth of rat glioblastoma although displaying modest survival improvement [41]. At this point, it is possible that therapies targeting multiple coagulation steps, including the FVIIa/TF complex, may offer better results. In the case of Ixolaris, further studies employing an orthotopic model (intracerebral administration of tumor cells) may reinforce this hypothesis. This model will be also important for evaluating the risk of intracranial bleeding, which is an important side-effect of the antithrombotic therapy in glioma patients [42].

There is a high incidence of thrombotic events throughout the course of malignant glioma [43]. More recently, tumoral intravascular thrombosis was reported as a distinguishing feature between glioblastoma—the most aggressive primary brain tumor—and lower grade astrocytomas [44]. In fact, the prothrombotic properties of glioblastoma cells seem to contribute to the appearance of hypoxic regions within the tumor [21] and, ultimately, to the formation of necrotic foci that are well-recognized predictors of poor prognosis [45]. This hypothesis is supported by the observations that: (i) exposure of human glioma cell lines to hypoxia markedly increases TF expression, resulting in higher procoagulant activity [20]; and (ii) patients' specimens show increased TF expression in cells surrounding the necrotic foci ('pseudopalisading' cells) [20].

Herein it is demonstrated that the human U87-MG glioblastoma cell line also displays TF and PS on their surface, resulting in high procoagulant activity in vitro. Notably, TF is determinant for the in vitro coagulant activity of U87-MG cells. However, it is possible that in the tumor microenvironment context, PS contributes in vivo to the elevated occurrence of intra-tumoral thrombosis in high-grade gliomas.

Vaso-occlusive and prothrombotic mechanisms seem to be intimately related to tumor hypoxia, necrosis, and accelerated growth in glioblastoma [21]. In fact, intense angiogenesis is a distinguishing pathological hallmark of glioblastomas relative to lower-grade gliomas. Actually, glioblastoma is one of the most highly vascularized malignant tumors and there is strong evidence that VEGF plays a key role in this process [46]. In this regard, our data show that inhibition of glioblastoma growth by Ixolaris is accompanied by a significant downregulation of VEGF and angiogenesis in tumor mass. Given the known antithrombotic properties of Ixolaris [28], it is possible that suppression of angiogenesis derives at least in part, from reduction of intratumoral thrombosis, which could in turn decrease the hypoxic regions within tumor mass and hypoxia driven VEGF production. In addition, other tumor models demonstrate decreased angiogenesis upon inhibition of TF, including carcinoma [36], colorectal [37] and breast cancer [38,40], and melanoma [47].

The involvement of TF on tumor angiogenesis might be coupled to activation of protease-activated receptors (PARs) by coagulation enzymes generated in the tumor microenvironment [17,18]. Binding of FVIIa to TF-expressing tumor cells may elicit signal transduction through PAR-2 activation followed by upregulation in VEGF expression [48]. In fact, it has been recently demonstrated that PAR-2 contributes to the angiogenic switch during mammary tumor development [49]. On the other hand, Yin et al. [50] have demonstrated that PAR-1 mediates angiogenesis, through VEGF production, in carcinoma and melanoma models. In addition, thrombin-mediated activation of PAR-1 in U87-MG cells increases VEGF transcription and expression [51]. Taken together, the effect of Ixolaris on tumor growth and angiogenesis may additionally result from decreased activation of PAR-1 and/or PAR-2 in U87-MG cells. This mechanism remains to be determined.

In conclusion, Ixolaris is a potent anticoagulant that does not produce major bleeding when injected subcutaneously in different animal models [28,52]. Remarkably, Ixolaris is non-immunogenic molecule (unpublished observations) and displays long half-life (>24 h, [28]). In addition, Ixolaris is effective at 50-250 µg kg$^{-1}$, doses that are two to three orders of magnitude lower than other molecules affecting TF or the coagulation cascade in the context of experimental therapeutics for cancer [38,41]. Finally, Ixolaris is an angiogenesis inhibitor that effectively suppresses tumor vessel formation in vivo. Accordingly, Ixolaris may attenuate the procoagulant state of cancer patients on one hand, and prevent angiogenesis on the other, thus interfering with two important components that contribute to tumor growth and metastasis in vivo.

Methods

The above-described examples were carried out with, but not limited only to, the methods and materials described below.

Materials

Recombinant Ixolaris was produced in High Five insect cells (Invitrogen, San Diego, Calif., USA), purified, and quantified as previously described [28]. Human thrombin and prothrombin were purified following previously reported procedures [29]. FXa was purchased from Calbiochem (San Diego, Calif., USA). Human FVa, FX, dansyl-Glu-Gly-Arg (DEGR)-FVIIa and placental annexin V were purchased from Haematologic Technologies (Essex Junction, Vt., USA). Human FIXa and FVIIa were purchased from American Diagnostica (Greenwich, Conn., USA). Human FVIII (Advate) was from Baxter Healthcare Corporation (Westlake Village, Calif., USA). FVIII was activated with human thrombin. Chromogenic substrates for FXa (S-2765, N-a-benzyloxy-carbonyl-D-Arg-Gly-Arg-p-nitroanilide) and thrombin (H-D-phenylalanyl-L-pipecolyl-L-arginine-p-nitroaniline dihydrochloride, S-2238) were purchased from Diapharma (Westchester, Ohio, USA).

Cell Culture

The human glioblastoma cell line, U87-MG, was grown at 37° C. in a humidified, 5% CO2 atmosphere in culture flasks, by subconfluent passages in Dulbeccos Modified Eagle Medium (DMEM-F12) (GibcoBRL; Invitrogen, Carlsbad, Calif., USA) supplemented with 2 g L$^{-1}$ HEPES, 60 mg L$^{-1}$ penicillin, 100 mg L$^{-1}$ streptomycin and 1.2 g L$^{-1}$ sodium bicarbonate.

Subconfluent cultures were washed twice with PBS, and cells were detached with Hank's solution containing 10 mM HEPES and 0.2 mM EDTA, spun at 350×g for 7 min, resuspended in supplemented DMEM-F12 and transferred at a 1:10 ratio to another culture flask. In all experiments, cells were resuspended in phosphate buffer-saline (PBS).

Flow Cytometric Analysis

Cells grown in culture were resuspended in phosphate buffered saline containing 0.1% BSA and incubated for 15 min, at 4° C., with murine monoclonal antibodies against human TF (4503, American Diagnostica, Stamford, Conn., USA). After washing to remove unbound antibody, cells were incubated with goat anti-mouse IgG conjugated with FITC (Santa Cruz Biotechnology, Santa Cruz, Calif., USA). Cells were washed again and analyzed using a FACScalibur (Becton-Dickinson, San José, Calif., USA). Data were analyzed using the WINMDI 2.8 version software. For surface phosphatidylserine detection, U87-MG cells were resuspended in 150 mM NaCl, 5 mM KCl, 2.5 mM CaCl$_2$, 1 mM MgCl2 and 10 mM HEPES, pH 7.3 (annexin binding buffer), and incubated with 25 μg mL$^{-1}$ annexin V-FITC (Molecular Probes; Invitrogen) for 15 min at room temperature. U87-MG cells were also labeled with 10 μg mL$^{-1}$ propidium iodide (PI) for exclusion of those that had lost plasma membrane integrity, thus becoming PI permeable.

Factor Xa Generation Assays

Activation of FX to FXa by FVIIa was performed as described [30] in 50 mM HEPES, 100 mM NaCl, 5 mM CaCl2, 1 mg mL) 1 BSA, pH 7.5 (HEPES-BSA buffer), as follows. FVIIa (1 nM) was incubated for different time periods, at 37° C., with U87-MG cells (5×10$^5$ mL$^{-1}$ in the presence of 100 nM FX. After addition of 50 μL of 300 μM S-2765, prepared in 50 mM Tris-HCl, 150 mM NaCl, 10 mM EDTA, 1 mg mL$^{-1}$ PEG 6,000, pH 7.5 (Tris-EDTA buffer), absorbance at 405 nm was recorded, at 37° C., for 20 min at 6-s intervals using a Thermomax Microplate Reader (Molecular Devices, Menlo Park, Calif., USA) equipped with a microplate mixer and heating system. Velocities (mOD min$^{-1}$) obtained in the first minutes of reaction were used to calculate the amount of FXa formed. Controls performed in the absence of cells or in the absence of FVIIa showed no significant FXa formation. The inhibitory effect of Ixolaris was evaluated by preincubating FX with varying amounts of the inhibitor (0-10 nM) for 10 min, at 37° C., prior to adding it to FVIIa (1 nM) and U87-MG cells (5·105 mL)1). FXa formed in the absence of Ixolaris was taken as 100%. Activation of FX to FXa by FIXa was performed in HEPES-BSA buffer, using a previously described discontinuous assay [31]. FIXa (0.2 nM, final concentration) was incubated with FVIIIa (4 IU mL$^{-1}$, final concentration) in the presence of U87-MG cells (5×10$^5$ mL$^{-1}$) for 5 min at 37° C. Reaction was initiated by addition of FX (100 nM, final concentration) and aliquots of 25 μL were removed every 2 min and placed into microplate wells containing 25 μL of Tris-EDTA buffer. After addition of 50 μL of 200 μM S-2765 prepared in Tris-EDTA buffer, absorbance at 405 nm was recorded, at 37° C., for 20 min at 6-s intervals as described above. Negative controls were performed in the absence of cells or in the absence of FVIIIa, showing no significant FXa formation. In some cases, FX was previously incubated with varying amounts (0-100 nM) of Ixolaris for 10 min, at 37° C., and FXa formed in the absence of the inhibitor was taken as 100%.

Thrombin Generation Assay

Activation of prothrombin by the prothrombinase complex (FXa/FVa) was performed in HEPES-BSA buffer, using a discontinuous assay [31]. FXa (10 pM, final concentration) was incubated with FVa (1 nM, final concentration) in the presence of U87-MG cells (5·105 mL)1) for 2 min at 37° C. Reaction was initiated by the addition of prothrombin (0.5 μM, final concentration) and aliquots of 10 μL were removed every 1 min into microplate wells containing 25 μL of Tris-EDTA buffer. After addition of 50 μL of 400 μM S-2238 prepared in Tris-EDTA buffer, absorbance at 405 nm was recorded, at 37° C., for 20 min at 6-s intervals using a Thermomax Microplate Reader. Velocities (mOD min$^{-1}$) obtained in the first minutes of reaction were used to calculate the amount of thrombin formed. Negative controls were carried out in the absence of cells or in the absence of FVa, showing no significant thrombin formation. Inhibitory effects of Ixolaris upon the prothrombinase complex were tested by preincubating FXa with varying amounts of Ixolaris (0-4 nM) for 10 min, at 37° C., in HEPES-BSA buffer.

Inhibition of Coagulant Complexes by Annexin V

The effect of annexin V on thrombin or FXa formation was tested as follows: U87-MG cells (5·105 mL)1) were incubated with varying amounts of annexin V (0-5 nM) for 5 min at 37° C. in HEPES-BSA buffer. Cells were then incubated with either FXa (10 pM)/prothrombin (0.5 lM), or FIXa (0.2 nM)/FX (100 nM) followed by the addition of FVa (1 nM) or FVIIIa (4 IU mL$^{-1}$), respectively. Aliquots of 25 μL were removed after 2 min, and delivered to microplate wells containing 25 μL of Tris-EDTA buffer. The amount of FXa or thrombin formed was evaluated as described above, using S-2238 or S-2765, respectively.

Procoagulant Activity Measured by Recalcification Time

The ability of U87-MG glioblastoma cells to potentiate plasma coagulation was assessed by measuring the recalcification time on an Amelung KC4A coagulometer (Labcon, Heppenheim, Germany) using plastic tubes. Human blood samples were collected from healthy donors in 3.8% trisodium citrate (9:1, v/v), and platelet-poor plasma was obtained by further centrifugation at 2000×g for 10 min. Plasma was incubated with 50 μL of U87-MG glioblastoma cells at various concentrations (suspension in TBS buffer) for 1 min at 37° C. Plasma clotting was initiated by the addition of 100 μL of 12.5 mM CaCl$_2$ and the time for clot formation was then recorded. In some cases, cells were previously incubated with the inactivated form of FVIIa, DEGR-FVIIa, for 10 min at room temperature. The in vitro effect of Ixolaris on U87-MG-induced coagulation was evaluated using the following procedure: plasma (50 μL) was incubated with Ixolaris (10 μL) for 10 min at 37° C., followed by the addition of 100 IL of 12.5 mM CaCl2.

Tumor Growth Assay

U87-MG cells (2×10$^6$) were subcutaneously inoculated into the flank of 6-week-old, male Balb/C nude mice (Chemistry Institute Animal Room, Sao Paulo University, Sao Paulo, Brazil). Treatment with Ixolaris (diluted in PBS, 100 μL final volume) was initiated 3 days after tumor cell inoculation and continued daily for 17 days. Control animals received PBS instead of the inhibitor. Treatment was performed by subcutaneous administration into the flank, preferentially at distant sites from tumor inoculation. Tumor growth was evaluated for 20 days with calipers, and the volume was calculated using the equation: (length)×(width)·(π/6). Preliminary analysis showed macroscopic necrotic areas in some control animals after 20 days of cell inoculation. Tumor weight was determined at the time of sacrifice. Analysis of variance (ANOVA) was used to establish differences between groups, and significance levels were determined by nonparametric Mann-Whitney test. Animal experiments were performed under approved protocols of the institutional animal use and care committee.

RNA Isolation and Reverse Transcriptase Real-Time PCR

Tumor RNA was isolated using the Trizol reagent (Invitrogen). After cDNA synthesis using Superscript III reverse transcriptase (Invitrogen), mRNA levels were determined by quantitative polymerase chain reaction (PCR) on a GeneAmp 7300 Sequence Detection System (Applied Biosystems, Foster City, Calif., USA) using SYBR Green Master mix and sequence-specific primers designed using Primer Express 3 (Applied Biosystems). Primers used were: VEGF (F: 5'-AGTGGTGAAGTTCATGGATGT-3', R: 5'-GCACA-CAGGATGGCTTGAAGA-3') and GAPDH (F: 5'-CCCACTCCTCCACCTTTGA-3', R: 5'-CTGTTGCTG-TAGCCAAA TTCGT-3').

Immunohistochemistry

Tissue staining was performed on paraffin-embedded sections (4-lm thick), which were incubated overnight, following heat antigen retrieval, with primary antibodies: monoclonal antimouse endoglin (CD105) antibody (MAB-1320, R&D Systems, Minneapolis, Minn., USA) at 1:20 dilution, or monoclonal antibody against VEGF (SC-7269, Santa Cruz Biotechnology) at 1:100 dilution. In order to reduce non-specific antibody binding, sections were incubated with PBS containing 10% non-immune goat serum, 5% BSA and 10% fetal bovine serum for 30 min prior to incubation with primary antibodies. Sections were further revealed using the LSAB2 Kit, HRP (Dako-Cytomation, Carpinteria, Calif., USA) with diaminobenzidine (3,3'-diaminobenzidine tablets; Sigma Chemical Co, St Louis, Mo., USA) as the chromogen and counterstained with hematoxylin. Negative control slides consisted of sections incubated with antibody vehicle or non-immune rat or mouse serum. Ten fields of immunostained section (CD105 and VEGF) were chosen at random and captured from each specimen. Quantification was assessed on captured high quality images (2048·1536 pixels buffer) using IMAGE PRO PLUS 4.5.1 (Media Cybernetics, Silver Spring, Md., USA). Data were stored in Adobe Photoshop, version 3.0 (Adobe Systems Inc., San Jose, Calif., USA), to enable uneven illumination and background color to be corrected. The number of transversal sections of CD105 was counted, and these numbers per square millimeter of the tumor were calculated, as previously described [32]. A semi-quantitative evaluation of immunohistochemical staining for VEGF was performed as described [32]. Statistical analyses comparing control and treatment groups used one-way ANOVA. Values of P<0.05 were considered to be statistically significant.

REFERENCES

1. Gomez K, McVey J H. Tissue factor initiated blood coagulation. Front Biosci 2006; 11: 1349-59.
2. Kalafatis M, Swords N A, Rand M D, Mann K G. Membrane-dependent reactions in blood coagulation: role of the vitamin K-dependent enzyme complexes. Biochim Biophys Acta 1994; 1227: 113-29.
3. Monroe D M, Hoffman M, Roberts H R. Platelets and thrombin generation. Arterioscler Thromb Vasc Biol 2002; 22: 1381-9.
4. Østerud B, Bjørklid E. Sources of tissue factor. Semin Thromb Hemost 2006; 32: 11-23.
5. Ruf W, Edgington T S. Structural biology of tissue factor, the initiator of thrombogenesis in vivo. FASEB J 1994; 8: 385-90.
6. Francischetti I M, Seydel K B, Monteiro R Q. Blood coagulation, inflammation, and malaria. Microcirculation 2008; 15: 81-107.
7. Buller H R, van Doormaal F F, van Sluis G L, Kamphuisen P W. Cancer and thrombosis: from molecular mechanisms to clinical presentations. J Thromb Haemost 2007; 5(Suppl. 1): 246-54.
8. Zwicker J I, Furie B C, Furie B. Cancer-associated thrombosis. Crit Rev Oncol Hematol 2007; 62: 126-36.
9. Kakkar A K, Lemoine N R, Scully M F, Tebbutt S, Williamson R C. Tissue factor expression correlates with histological grade in human pancreatic cancer. Br J Surg 1995; 82: 1101-4.
10. Hamada K, Kuratsu J, Saitoh Y, Takeshima H, Nishi T, Ushio Y. Expression of tissue factor correlates with grade of malignancy in human glioma. Cancer 1996; 77: 1877-83.
11. Guan M, Jin J, Su B, Liu W W, Lu Y. Tissue factor expression and angiogenesis in human glioma. Clin Biochem 2002; 35: 321-5.
12. Nakasaki T, Wada H, Shigemori C, Miki C, Gabazza E C, Nobori T, Nakamura S, Shiku H. Expression of tissue factor and vascular endothelial growth factor is associated with angiogenesis in colorectal cancer. Am J Hematol 2002; 69: 247-54.
13. Zhang Y, Deng Y, Luther T, Muller M, Ziegler R, Waldherr R, Stern D M, Nawroth P P. Tissue factor controls the balance of angiogenic and antiangiogenic properties of tumor cells in mice. J Clin Invest 1994; 94: 1320-7.
14. Abe K, Shoji M, Chen J, Bierhaus A, Danave I, Micko C, Casper K, Dillehay D L, Nawroth P P, Rickles F R. Regulation of vascular endothelial growth factor production and angiogenesis by the cytoplasmic tail of tissue factor. Proc Natl Acad Sci USA 1999; 96: 8663-8.
15. Rak J, Milsom C, May L, Klement P, Yu J. Tissue factor in cancer and angiogenesis: the molecular link between genetic tumor progression, tumor neovascularization, and cancer coagulopathy. Semin Thromb Hemost 2006; 32: 54-70.
16. Khorana A A, Ahrendt S A, Ryan C K, Francis C W, Hruban R H, Hu Y C, Hostetter G, Harvey J, Taubman M B. Tissue factor expression, angiogenesis, and thrombosis in pancreatic cancer. Clin Cancer Res 2007; 13: 2870-5.
17. Belting M, Ahamed J, Ruf W. Signaling of the tissue factor coagulation pathway in angiogenesis and cancer. Arterioscler Thromb Vasc Biol 2005; 25: 1545-50.
18. Rao L V, Pendurthi U R. Tissue factor-factor VIIa signaling. Arterioscler Thromb Vasc Biol 2005; 25: 47-56.
19. Behin A, Hoang-Xuan K, Carpentier A F, Delattre J Y. Primary brain tumours in adults. Lancet 2003; 361: 323-31.
20. Rong Y, Post D E, Pieper R O, Durden D L, Van Meir E G, Brat D J. PTEN and hypoxia regulate tissue factor expression and plasma coagulation by glioblastoma. Cancer Res 2005; 65: 1406-13.
21. Brat D J, Van Meir E G. Vaso-occlusive and prothrombotic mechanisms associated with tumor hypoxia, necrosis, and accelerated growth in glioblastoma. Lab Invest 2004; 84: 397-405.
22. Rong Y, Durden D L, Van Meir E G, Brat D J. Pseudopalisading necrosis in glioblastoma: a familiar morphologic feature that links vascular pathology, hypoxia, and angiogenesis. J Neuropathol Exp Neurol 2006; 65: 529-39.
23. Ornstein D L, Meehan K R, Zacharski L R. The coagulation system as a target for the treatment of human gliomas. Semin Thromb Hemost 2002; 28: 19-28.
24. Francischetti I M, Valenzuela J G, Andersen J F, Mather T N, Ribeiro J M. Ixolaris, a novel recombinant tissue factor pathway inhibitor (TFPI) from the salivary gland of the tick, *Ixodes scapularis*: identification of factor X and factor Xa as scaffolds for the inhibition of factor VIIa/tissue factor complex. Blood 2002; 99: 3602-12.
25. Broze G J Jr. Tissue factor pathway inhibitor and the revised theory of coagulation. Annu Rev Med 1995; 46: 103-12.
26. Monteiro R Q, Rezaie A R, Ribeiro J M, Francischetti I M. Ixolaris: a factor Xa heparin-binding exosite inhibitor. Biochem J 2005; 387: 871-7.
27. Monteiro R Q, Rezaie A R, Bae J S, Calvo E, Andersen J F, Francischetti I M. Ixolaris binding to factor X reveals a precursor state of factor Xa heparin-binding exosite. Protein Sci 2008; 17: 146-53.
28. Nazareth R A, Tomaz L S, Ortiz-Costa S, Atella G C, Ribeiro J M, Francischetti I M, Monteiro R Q. Antithrombotic properties of Ixolaris, a potent inhibitor of the extrinsic pathway of the coagulation cascade. Thromb Haemost 2006; 96: 7-13.

29. Monteiro R Q, Bock P E, Bianconi M L, Zingali R B. Characterization of bothrojaracin interaction with human prothrombin. Protein Sci 2001; 10: 1897-904.
30. Geaquinto D L, Fernandes R S, Lima L G, Barja-Fidalgo C, Monteiro R Q. Procoagulant properties of human MV3 melanoma cells. Braz J Med Biol Res 2008; 41: 99-105.
31. Fernandes R S, Kirszberg C, Rumjanek V M, Monteiro R Q. On the molecular mechanisms for the highly procoagulant pattern of C6 glioma cells. J Thromb Haemost 2006; 4: 1546-52.
32. Machado D E, Abrao M S, Berardo P T, Takiya C M, Nasciutti L E. Vascular density and distribution of vascular endothelial growth factor (VEGF) and its receptor VEGFR-2 (Flk-1) are significantly higher in patients with deeply infiltrating endometriosis affecting the rectum. Feral Steril 2008; 90: 148-55.
33. Bastida E, Ordinas A, Escolar G, Jamieson G A. Tissue factor in microvesicles shed from U87MG human glioblastoma cells induces coagulation, platelet aggregation, and thrombogenesis. Blood 1984; 64: 177-84.
34. Connor J, Bucana C, Fidler L T, Schroit A J. Differentiation-dependent expression of phosphatidylserine in mammalian plasma membranes: quantitative assessment of outer-leaflet lipid by prothrombinase complex formation. Proc Natl Acad Sci USA 1989; 86: 3184-8.
35. VanDeWater L, Tracy P B, Aronson D, Mann K G, Dvorak H F. Tumor cell generation of thrombin via functional prothrombinase assembly. Cancer Res 1985; 45: 5521-5.
36. Milsom C C, Yu J L, Mackman N, Micallef J, Anderson G M, Guha A, Rak J W. Tissue factor regulation by epidermal growth factor receptor and epithelial-to-mesenchymal transitions: effect on tumor initiation and angiogenesis. Cancer Res 2008; 68: 10068-76.
37. Zhao J, Aguilar G, Palencia S, Newton E, Abo A. rNAPc2 inhibits colorectal cancer in mice through tissue factor. Clin Cancer Res 2009; 15: 208-16.
38. Ngo C V, Picha K, McCabe F, Millar H, Tawadros R, Tam S H, Nakada M T, Anderson G M. CNTO 859, a humanized anti-tissue factor monoclonal antibody, is a potent inhibitor of breast cancer metastasis and tumor growth in xenograft models. Int J Cancer 2007; 120: 1261-7.
39. Yu J, May L, Milsom C, Anderson G M, Weitz J I, Luyendyk J P, Broze G, Mackman N, Rak J. Contribution of host-derived tissue factor to tumor neovascularization. Arterioscler Thromb Vasc Biol 2008; 28: 1975-81.
40. Versteeg H H, Schaffner F, Kerver M, Petersen H H, Ahamed J, Felding-Habermann B, Takada Y, Mueller B M, Ruf W. Inhibition of tissue factor signaling suppresses tumor growth. Blood 2008; 111: 190-9.
41. Hua Y, Tang L, Keep R F, Schallert T, Fewel M E, Muraszko K M, Hoff J T, Xi G. The role of thrombin in gliomas. J Thromb Haemost 2005; 3: 1917-23.
42. Altschuler E, Moosa H, Selker R G, Vertosick F T Jr. The risk and efficacy of anticoagulant therapy in the treatment of thromboembolic complications in patients with primary malignant brain tumors. Neurosurgery 1990; 27: 74-7.
43. Marras L C, Geerts W H, Perry J R. The risk of venous thromboembolism is increased throughout the course of malignant glioma: an evidence-based review. Cancer 2000; 89: 640-6.
44. Tehrani M, Friedman T M, Olson J J, Brat D J. Intravascular thrombosis in central nervous system malignancies: a potential role in astrocytoma progression to glioblastoma. Brain Pathol 2008; 18: 164-71.
45. Barker F G II, Davis R L, Chang S M, Prados M D. Necrosis as a prognostic factor in glioblastomamultiforme. Cancer 1996; 77: 1161-6.
46. Plate K H, Breier G, Weich H A, Risau W. Vascular endothelial growth factor is a potential tumour angiogenesis factor in human gliomas in vivo. Nature 1992; 359: 845-8.
47. Hembrough T A, Swartz G M, Papathanassiu A, Vlasuk G P, Rote W E, Green S J, Pribluda V S. Tissue factor/factor VIIa inhibitors block angiogenesis and tumor growth through a nonhemostatic mechanism. Cancer Res 2003; 63: 2997-3000.
48. Liu Y, Mueller B M. Protease-activated receptor-2 regulates vascular endothelial growth factor expression in MDA-MB-231 cells via MAPK pathways. Biochem Biophys Res Commun 2006; 344: 1263-70.
49. Versteeg H H, Schaffner F, Kerver M, Ellies L G, Andrade-Gordon P, Mueller B M, Ruf W. Protease-activated receptor (PAR) 2, but not PAR1, signaling promotes the development of mammary adenocarcinoma in polyoma middle T mice. Cancer Res 2008; 68: 7219-27.
50. Yin Y J, Salah Z, Maoz M, Ram S C, Ochayon S, Neufeld G, Katzav S, Bar-Shavit R. Oncogenic transformation induces tumor angiogenesis: a role for PAR1 activation. FASEB J 2003; 17: 163-74.
51. Yamahata H, Takeshima H, Kuratsu J, Sarker K P, Tanioka K, Wakimaru N, Nakata M, Kitajima I, Maruyama I. The role of thrombin in the neo-vascularization of malignant gliomas: an intrinsic modulator for the up-regulation of vascular endothelial growth factor. Int J Oncol 2002; 20: 921-8.
52. Waddington S N, McVey J H, Bhella D, Parker A L, Barker K, Atoda H, Pink R, Buckley S M, Greig J A, Denby L, Custers J, Morita T, Francischetti I M, Monteiro R Q, Barouch D H, van Rooijen N, Napoli C, Havenga M J, Nicklin S A, Baker A H. Adenovirus serotype 5 hexon mediates liver gene transfer. Cell 2008; 132: 397-409.
53. Broze, G. J. et al. 1990 Biochemistry 29:7539-7546.
54. Sprecher, C. A. et al. 1994 PNAS USA 91:3353-3357.
55. Laskowski, M. Jr. and Kato I. 1980 Annu Rev Biochem 49:593-626.
56. Wesselschmidt, R. et al. 1992 Blood 79:2004-2010.
57. Nordfang, O. et al. 1991 Biochemistry 30:10371-10376.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting growth of a cell expressing tissue factor (TF), comprising contacting the cell with an effective amount of an Ixolaris polypeptide such that the growth of the cell is inhibited, wherein the amount of Ixolaris polypeptide is 1-250 ug $kg^{-1}$, wherein the Ixolaris polypeptide is at least 95% identical to SEQ ID NO: 2.

2. A method of treating a TF mediated or associated disease or process in a subject, comprising administering to the subject an Ixolaris polypeptide in an amount effective to treat the TF mediated or associated disease or process, wherein the amount of Ixolaris polypeptide is 1-250 ug $kg^{-1}$, wherein the Ixolaris polypeptide is at least 95% identical to SEQ ID NO: 2.

3. A method of treating a tumor in a subject, comprising administering to the subject an Ixolaris polypeptide in an amount effective to treat the tumor, wherein the amount of Ixolaris polypeptide is 1-250 ug $kg^{-1}$, wherein the Ixolaris polypeptide is at least 95% identical to SEQ ID NO: 2.

4. The method of claim 1, wherein the cells are selected from the group consisting of: tumor cells, endothelial cells, vascular smooth muscle cells, inflammatory cells, or a combination thereof.

5. The method of claim 2, wherein the disease is selected from the group consisting of: cancer and a vascular disease.

6. The method of claim 3, wherein the tumor comprises a solid tumor.

7. The method of claim 3, wherein the tumor comprises a central nervous system tumor or a squamous cell tumor.

8. The method of claim 6, wherein the tumor is a glioblastoma.

9. The method of claim 7, wherein the tumor is a melanoma.

10. The method of claim 6, wherein the tumor is a metastatic tumor.

11. The method of claim 3, wherein the method decreases the rate of tumor growth, inhibits tumor growth, shrinks the tumor, or reduces tumor burden.

12. The method of claim 11, wherein one or more tumor markers are a sign or symptom associated with the presence of a tumor.

13. A method of treating cancer in a subject comprising administering to the subject an Ixolaris polypeptide in an amount effective to treat the cancer, wherein the amount of Ixolaris polypeptide is 1-250 ug $kg^{-1}$, wherein the Ixolaris polypeptide is at least 95% identical to SEQ ID NO: 2.

14. The method of claim 1, wherein the Ixolaris polypeptide is identical to SEQ ID NO: 2.

15. The method of and one of claim 1, 2, 3 or 13, wherein the amount of Ixolaris polypeptide is 50 ug $kg^{-1}$.

16. The method of and one of claim 1, 2, 3 or 13, wherein the amount of Ixolaris polypeptide is 250 ug $kg^{-1}$.

17. The method of claim 1, wherein the amount of Ixolaris polypeptide is 25-250 ug $kg^{-1}$.

18. The method of claim 2, wherein the amount of Ixolaris polypeptide is 25-250 ug $kg^{-1}$.

19. The method of claim 3, wherein the amount of Ixolaris polypeptide is 25-250 ug $kg^{-1}$.

20. The method of claim 13, wherein the amount of Ixolaris polypeptide is 25-250 ug $kg^{-1}$.

21. The method of any one of claims 17-20, wherein the amount of Ixolaris polypeptide is 50-250 ug $kg^{-1}$.

* * * * *

SEQUENCE LISTING

<160> NUMBER OF SEQ ID NOS: 7

<210> SEQ ID NO 1
<211> LENGTH: 295
<212> TYPE: PRT
<213> ORGANISM: Homo sapiens

<400> SEQUENCE: 1

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
        50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
        210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
        290                 295

<210> SEQ ID NO 2
<211> LENGTH: 165
<212> TYPE: PRT
<213> ORGANISM: Ixodes scapularis

<400> SEQUENCE: 2

```
Met Arg Ala Val Ser Cys Phe Leu Tyr Tyr Gly Val Ala Trp Ile Ala
1               5                   10                  15

Leu Gly Ser Trp Gly Ala Ser Ser Ala Glu Arg Val Ser Glu Met
            20                  25                  30

Asp Ile Tyr Glu Phe Glu Ser Trp Val Ser Cys Leu Asp Pro Glu Gln
            35                  40                  45

Val Thr Cys Glu Ser Gln Glu Gly Thr His Ala Ser Tyr Asn Arg Lys
        50                  55                  60

Thr Gly Gln Cys Glu Gln Lys Gly Thr Glu Cys Gly Gly Glu
65                  70                  75                  80

Asn His Phe Glu Thr Leu Leu Lys Cys Asn Glu Ser Cys Asn Asp Ala
                85                  90                  95

Pro Lys Pro Pro Cys Ser Leu Glu Val Asp Tyr Gly Val Gly Arg Ala
            100                 105                 110

Asn Ile Pro Arg Trp Tyr Tyr Asp Thr Asn Asn Ala Thr Cys Glu Met
            115                 120                 125

Phe Thr Tyr Gly Gly Ile Thr Gly Asn Lys Asn Asn Phe Glu Ser Glu
            130                 135                 140

Glu Glu Cys Lys Glu Thr Cys Lys Gly Phe Ser Leu Leu Lys Lys Val
145                 150                 155                 160

Asn Val Thr Ile Asn
                165
```

<210> SEQ ID NO 3
<211> LENGTH: 497
<212> TYPE: DNA
<213> ORGANISM: Ixodes scapularis

<400> SEQUENCE: 3

```
atgcgcgctg tttcctgctt cctatattat ggagttgctt ggattgcact tggaagttgg    60
ggtgcgtcaa gttcagcaga acgtgttagc gaaatggaca tctatgagtt cgaatcctgg   120
gtatcttgtc ttgatcccga caagtaacg tgtgaaagcc aagagggaac gcacgcttca    180
tacaaccgaa aaacgggaca gtgtgaagag caaaagggaa cagagtgtgg aggaggcgag   240
aatcactttg aaactttgtt gaagtgcaac gaatcttgca acgatgctcc gaagccacct   300
gctcgctgga agtagattat ggtgttggaa gagctaacat accacgatgg tattatgaca   360
ccaacaatgc aacttgcgaa atgttcacct atggggaat aactggcaat aaaaacaatt    420
ttgaatccga ggaagagtgt aaggaaactt gcaagggttt ttctctgtta aagaaagtaa   480
atgtcactat taactga                                                  497
```

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 4

```
agtggtgaag ttcatggatg t                                              21
```

-continued

```
<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
gcacacagga tggcttgaag a                                            21

<210> SEQ ID NO 6
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
cccactcctc cacctttga                                               19

<210> SEQ ID NO 7
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
ctgttgctgt agccaaattc gt                                           22
```